US012570986B2

(12) United States Patent     (10) Patent No.:   US 12,570,986 B2

Guo et al.     (45) Date of Patent:    Mar. 10, 2026

(54) SEC12-LIKE PROTEIN GENE CPU1 AND APPLICATION THEREOF IN IMPROVING SOYBEAN PHOSPHORUS EFFICIENCY

(71) Applicant: Fujian Agriculture and Forestry University, Fuzhou (CN)

(72) Inventors: Zilong Guo, Fuzhou (CN); Zhichang Chen, Fuzhou (CN); Hong Liao, Fuzhou (CN)

(73) Assignee: Fujian Agriculture and Forestry University, Fuzhou (CN)

( * ) Notice: Subject to any disclaimer, the term of this patent is extended or adjusted under 35 U.S.C. 154(b) by 0 days.

(21) Appl. No.: 18/049,645

(22) Filed: Oct. 26, 2022

(65) Prior Publication Data

US 2023/0193290 A1     Jun. 22, 2023

(30) Foreign Application Priority Data

Oct. 26, 2021    (CN) .......................... 202111245060.6

(51) Int. Cl.
*C12N 15/52*     (2006.01)
*C12N 15/82*     (2006.01)

(52) U.S. Cl.
CPC ......... *C12N 15/52* (2013.01); *C12N 15/8261* (2013.01)

(58) Field of Classification Search
None
See application file for complete search history.

(56) References Cited

PUBLICATIONS

Schmutz et al., Genome Sequence of the Palaeopolyploid Soybean, 2010, Nature, 463.7278. Published online on Feb. 11, 2009. Sequence submitted to GenBank database with Accession No. NC_038256 and NC_016107 on Apr. 19, 2021 (Year: 2009).*
Schmutz et al., GenBank database (Accession No. NC_038256 and NC_016107) published on Apr. 19, 2021 (Year: 2021).*
NCBI Blast alignment for NC_038256.2 and SEQ ID No. 1 (Year: 2021).*
Malhotra et al., Phosphorus Nutrition: Plant Growth in Response to Deficiency and Excess, Plant Nutrients and Abiotic Stress Tolerance, Singapore: Springer, 2018. 171-190 (Year: 2018).*
Provin et al. Texas Cooperative extension, Texas A&M University system (website accessed on Aug. 8, 2025) (Year: 2025).*
Shi Hui, et al., Shift of Status:Comparative Study on the Development of Soybean in China and the United States, Agricultural History of China, 2018, pp. 56-62, vol. 5.
Li Xin-Xin, et al., Contributions of Symbiotic Nitrogen Fixation in Soybean to Reducing Fertiliza-tion While Increasing Efficiency in Agriculture, Soybean Science, 2016, pp. 531-535, vol. 35, No. 4.
Jeremy Schmutz, et al., Genome sequence of the palaeopolyploid soybean, Nature, 2010, pp. 178-183, vol. 463.
Hon-Ming Lam, et al., Resequencing of 31 wild and cultivated soybean genomes identifies patterns of genetic diversity and selection, Nature Genetics, 2010, pp. 1053-1059, vol. 42, No. 12.
Zhengkui Zhou, et al., Resequencing 302 wild and cultivated accessions identifies genes related to domestication and improvement in soybean, Nature Biotechnology, 2015, pp. 408-414,441, vol. 33, No. 4.
Chao Fang, et al., Genome-wide association studies dissect the genetic networks underlying agronomical traits in soybean, Genome Biology, 2017, pp. 1-13, vol. 18, No. 161.
Xiurong Wang, et al., Overexpressing AtPAP15 Enhances Phosphorus Efficiency in Soybean, Plant Physiology, 2009, pp. 233-240, vol. 151.
J. Murphy, et al., A Modified Single Solution Method for the Determination of Phosphate in Natural Waters, Analytica Chimica Acta, 1962, pp. 31-36, vol. 27.
SQL gene list, retrieved from: http://plants.ensembl.org/info/website/ftp/index.html.

* cited by examiner

*Primary Examiner* — Bratislav Stankovic
*Assistant Examiner* — Jay Chatterjee
(74) *Attorney, Agent, or Firm* — Jose Cherson Weissbrot

(57) ABSTRACT

A SEC12-like protein gene CPU1 and application thereof in improving soybean phosphorus efficiency are disclosed. Through genome-wide association studies, a major genetic locus affecting soybean phosphorus efficiency is identified, and the candidate gene CPU1 is discovered and validated. There are natural variations in gene CPU1 in soybean population, including two alleles, phosphorus-inefficient allele CPU1-H1 and phosphorus-efficient allele CPU1-H2. Studies based on CPU1-transformation plants shows that inhibiting the expression of the allele CPU1-H2 significantly reduces soybean phosphorus efficiency, and ultimately reduces the biomass and yield of transgenic plants. The present disclosure provides new scientific insights into genetic bases underlying natural phenotypic variation in crops, and provides novel allele resources for molecular breeding of phosphorus efficiency.

6 Claims, 5 Drawing Sheets

Specification includes a Sequence Listing.

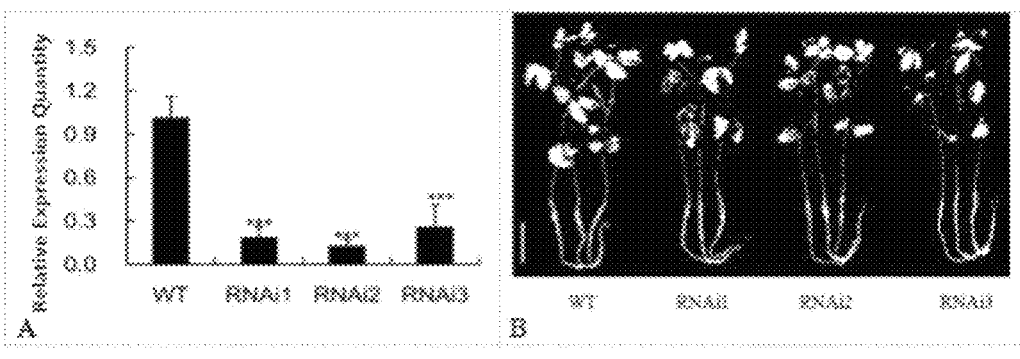
FIG. 2A                                         FIG. 2B
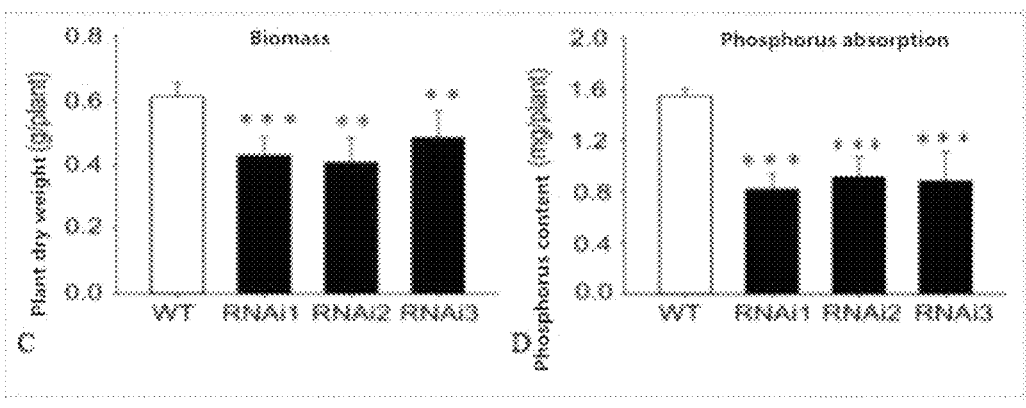
FIG. 2C                                         FIG. 2D
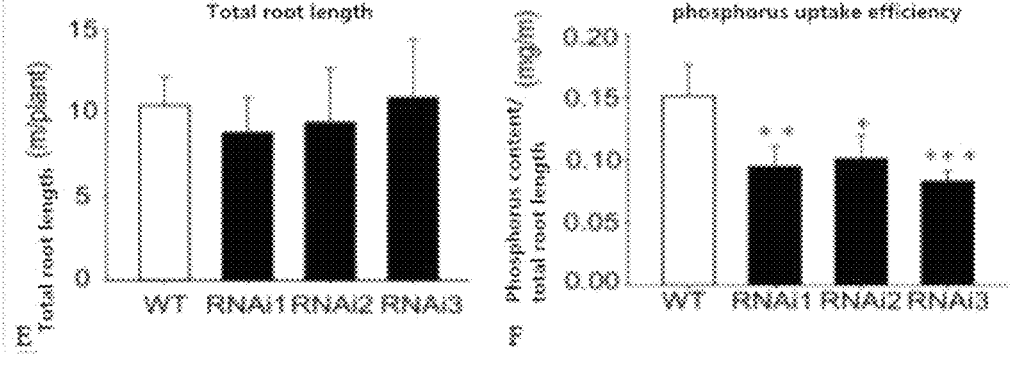
FIG. 2E                                         FIG. 2F

FIG. 2G                                    FIG. 2H

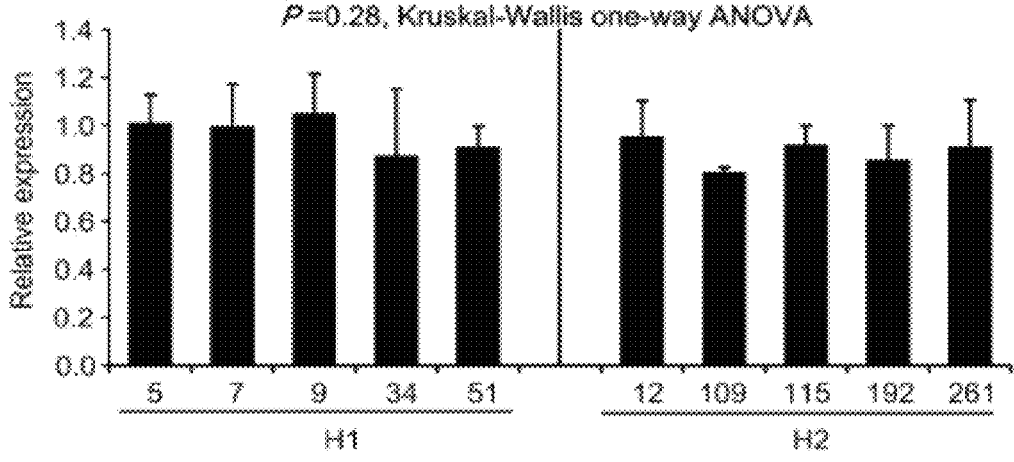
FIG. 4
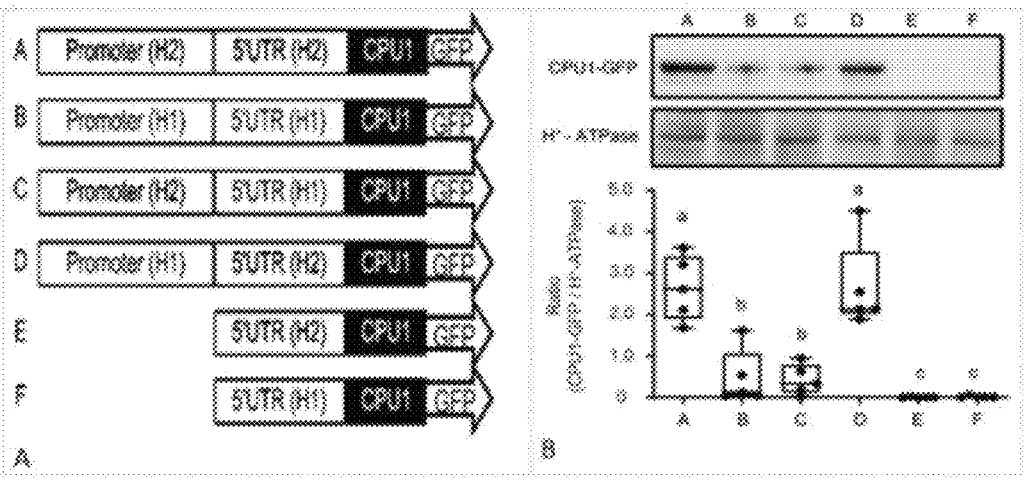
FIG. 5A                                        FIG. 5B

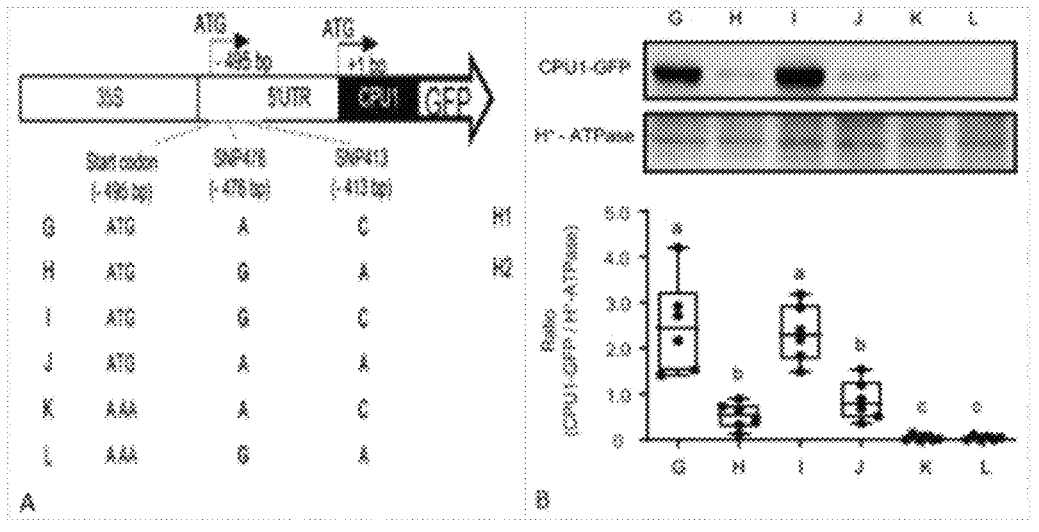
FIG. 6A                                                    FIG. 6B

SEC12-LIKE PROTEIN GENE CPU1 AND APPLICATION THEREOF IN IMPROVING SOYBEAN PHOSPHORUS EFFICIENCY

CROSS REFERENCE TO THE RELATED APPLICATIONS

The application is based upon and claims priority to Chinese Patent Application No: 202111245060.6, filed on Oct. 26, 2021, the entire contents of which are incorporated herein by reference.

SEQUENCE LISTING

The instant application contains a Sequence Listing which has been submitted in XML format via and is hereby incorporated by reference in its entirety. Said XML copy is named GBYC068-SEQUENCE_LISTING-20240711.xml, created on Jul. 11, 2024, and is 40,526 bytes in size.

TECHNICAL FIELD

The present invention relates to the field of biotechnology, particularly to a SEC12-like protein gene CPU1 and application thereof in improving soybean phosphorus efficiency.

BACKGROUND

As an important grain, oil and forage crop in China, soybean provides a lot of protein and oil. Although China is the origin of soybean, it was also the largest soybean producer, consumer and exporter in the world for a long time; however, since 1996, China has become a net importing country of soybeans. China needs to import a large amount of soybeans from the Americas every year, and there are serious hidden dangers in food security (Shi Hui et al., 2018). Meanwhile, as the leguminous crop with the largest biological nitrogen fixation, soybean promotes less fertilizer application, higher nutrient efficiency, and environmental pollution reduction (Li Xinxin et al., 2016). Therefore, improving China's soybean production capacity is of great significance in ensuring food security and sustainable ecological agricultural development.

Phosphorus is an essential mineral nutrient for plants and plays a vital role in the growth and development of plants. The phenomenon "P promoting N nutrition" exists in leguminous crops: phosphorus can promote nodulation and nitrogen fixation of leguminous crops, thus improving nitrogen efficiency. The main source of phosphorus is soil. The total phosphorus content in the soil is high, but most of it is insoluble inorganic phosphorus and organic phosphorus, which are difficult to be used by plants; and the mobility of phosphorus in the soil is poor. In actual agricultural production, in order to obtain high yield, it is often necessary to supplement phosphorus by applying a large amount of fertilization, which results in serious environmental pollution. Therefore, how to improve the phosphorus-efficiency of crops, so that crops can obtain stable yield under the condition of reduced fertilization or higher yield under the condition of the same fertilization, is an important scientific issue for the development of resource-saving and environment-friendly ecological agriculture.

In recent years, association analysis has received more and more attention from researchers for at least two reasons: (I) The natural population used in the association analysis has experienced a long-term recombinant event, so it will have high mapping resolution; (II) Natural populations harbors abundant genetic variation, which is helpful for analyzing the genetic basis of trait variation and identifying favorable alleles (Yu and Buckler, 2006). With the publication of the soybean reference genome sequence and the re-sequencing of soybean natural populations in recent years (Schmutz et al. 2010, Lam et al. 2010), genome-wide association study has been successfully carried out in soybean (Zhou et al. 2015, Fang et al. 2017).

However, there are few reports on analyzing the genetic basis of natural variation of phosphorus efficiency in soybean, and there is no report on cloning the major gene of soybean phosphorus efficiency through forward genetics.

SUMMARY

Because of such problems, the present invention provides a SEC12-like protein gene CPU1 and application thereof in improving soybean phosphorus efficiency. The inventors phenotyped a soybean core collection for phosphorus efficiency in the field. Then, the inventors obtained high-density molecular markers based on next-generation sequencing, carried out genome-wide association studies (GWAS), identified a major genetic locus controlling phosphorus acquisition efficiency, and identified a candidate gene CPU1.

The research based on CPU1-transformation plants showed that knocking-down the expression of CPU1 significantly reduced the phosphorus acquisition efficiency of soybean, and ultimately reduced the biomass and yield of transgenic plants, which confirmed the function of the gene in phosphorus acquisition efficiency.

The inventors found that CPU1 had sequence variation in natural soybean population, and a base substitution of its 5'UTR changed the translation efficiency of CPU1, thereby affecting the phosphorus acquisition efficiency of soybean; meanwhile, the inventors identified a phosphorus-efficient allele CPU1-H2.

To achieve the above object, the present invention adopts the following technical solutions:

A SEC12-like protein gene CPU1, wherein the SEC12-like protein gene CPU1 has a natural variation in Soybean, and includes two alleles, the two alleles are a phosphorus-inefficient allele CPU1-H1 and a phosphorus-efficient allele CPU1-H2; wherein the SEC12-like protein gene CPU1 has an upstream open reading frame (uORF) in a 5'UTR, wherein the upstream open reading frame uORF has two SNPs are located at a 20th bp (a genotype is A in the phosphorus-efficient allele CPU1-H2; G in the phosphorus-inefficient allele CPU1-H1) in uORF of the phosphorus-efficient allele CPU1-H2 and the phosphorus-inefficient allele CPU1-H1 are A and G respectively, and the genotype at 83 bp in uORF of the two alleles are C and A respectively; wherein the nucleotide sequence of the phosphorus-efficient allele CPU1-H2 is shown in SEQ ID No: 1, wherein the nucleotide sequence of the phosphorus-inefficient allele CPU1-H1 is shown in SEQ ID NO: 5.

The cDNA sequences of the two alleles of the above SEC12-like protein gene CPU1 are the same, as shown in SEQ ID NO: 2.

The nucleotide sequence of uORF for the above phosphorus-efficient allele CPU1-H2 is shown in SEQ ID NO: 3.

A plant expression vector, wherein the plant expression vector contains the above SEC12-like protein gene CPU1.

The above plant expression vector includes transgenic plants formed by recombinant transformation, also includes the expressed product of exogenous gene.

An application in improving soybean phosphorus efficiency of the above SEC12-like protein gene CPU1.

Further, in the above applications, inhibiting the expression of allele CPU1-H2 can reduce the phosphorus acquisition efficiency of soybean.

Further, in the above applications, inhibiting the expression of allele CPU1-H2 can reduce biomass and yield of soybean.

The present invention has the following advantages: The present invention provides a new gene SEC12-like protein gene CPU1 which can improve soybean phosphorus efficiency. CPU1 has sequence variation in the natural soybean population, and a base substitution of its 5'UTR changes the translation efficiency of CPU1, thus affecting the phosphorus acquisition efficiency of soybean. Meanwhile, the inventors identified the phosphorus-efficiency allele CPU1-H2. This study will help to comprehensively understand the genetic basis of soybean phosphorus efficiency, provide new scientific insights into the genetic basis of natural variation of crops, and provide phosphorus-efficient allele for molecular breeding, which will ultimately be of great significance for the development of environment-friendly, resource-saving and sustainable ecological agriculture.

BRIEF DESCRIPTION OF THE DRAWINGS

FIGS. 2A-2H. Effects of CPU1 on phosphorus acquisition efficiency, biomass and yield of soybean transgenic plants. FIG. 2A: Relative expression of CPU1 of three independent transgenic RNAi lines; FIG. 2B: Growth at seeding stage of RNAi lines and wild-type plants; FIG. 2C: Biomass at seedling stage of RNAi lines and wild-type plants; FIG. 2D: Phosphorus acquisition at seedling stage of RNAi lines and wild-type plants; FIG. 2E: Total root length at seedling stage of RNAi lines and wild-type plants; FIG. 2F: Phosphorus acquisition efficiency at seedling stage of RNAi lines and wild-type plants; FIG. 2G: Growth at maturity of RNAi lines and wild-type plants; FIG. 2H: Pods number per plant at maturity stage of RNAi lines and wild-type materials; * indicates $0.01 < P \leq 0.05$ and the difference is significant;  indicates $0.001 < P \leq 0.01$ and the significance of the difference is between significant and extremely significant; * indicates $P \leq 0.001$ and the difference is extremely significant.

FIG. 4. Comparison of the expression amounts of two alleles of CPU1.

FIGS. 5A-5B. Identification of causal variation region by construction of recombinant vectors and Western-blot. FIG. 5A: Recombinant vectors containing promoters and 5'UTR of different haplotypes; FIG. 5B: Western-blot results of soybean hairy roots transferred into six recombinant vectors in A; in multiple comparisons, different English letters represent significant differences (P<0.05).

FIGS. 6A-6B: Identification of causal variants by construction of recombinant vector and Western-blot. FIG. 6A: Diagram of recombinant vector containing 5'UTR of different genotypes; FIG. 6B: Western-blot results of soybean hairy roots transferred into the six recombinant vectors in (A); in multiple comparisons, different English letters represent significant differences (P<0.05).

DETAILED DESCRIPTION OF THE EMBODIMENTS

Figure 1:
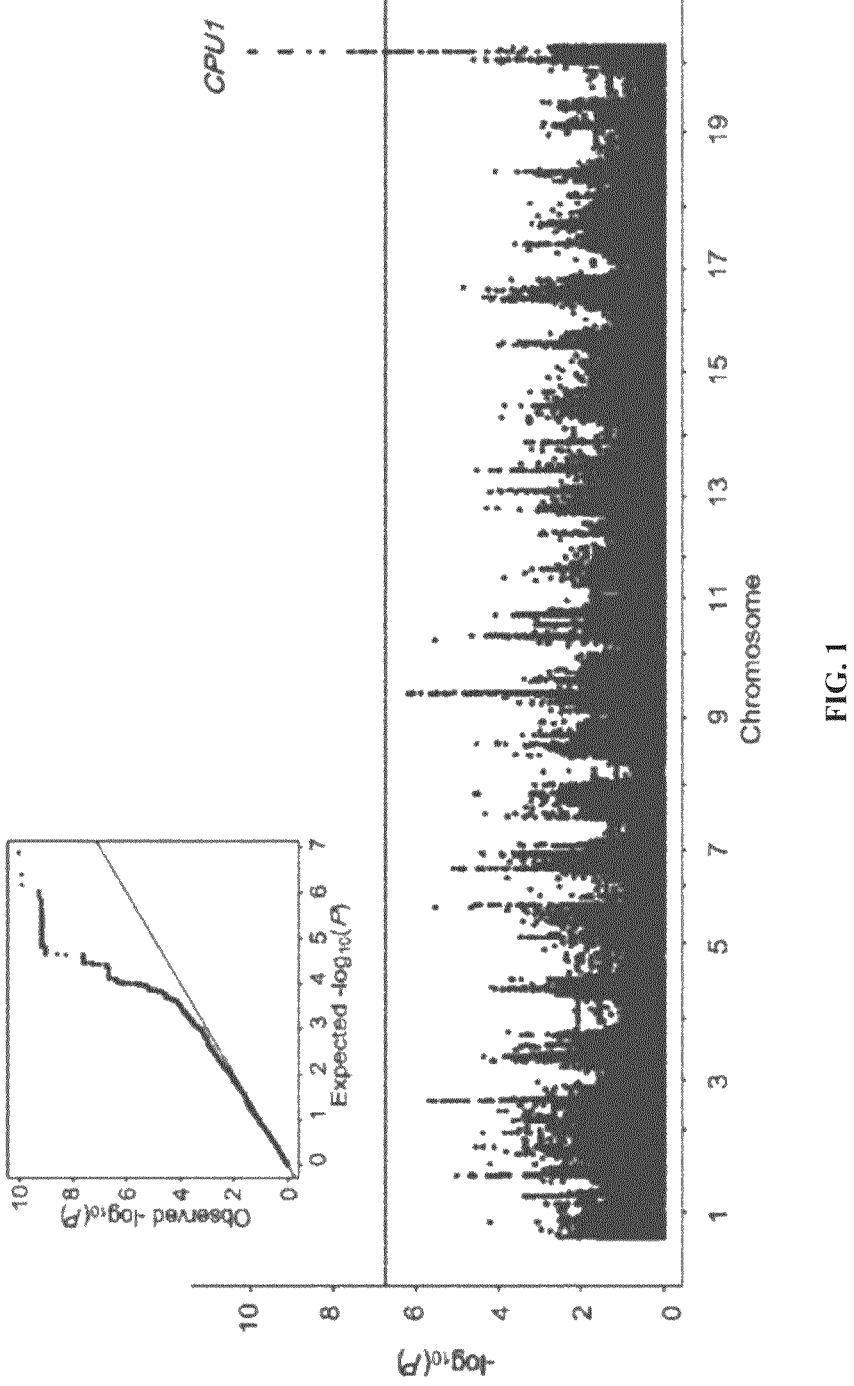
FIG. 1. Genome-wide association analysis results of phosphorus acquisition efficiency of soybean. At the upper left is a quantile-quantile plot, showing the control effect of population structure. At the bottom is a Manhattan plot, the x- and y-values correspond to the physical locations of SNP and the negative logarithm of P values respectively, the horizontal line in the figure represents the significance threshold of association analysis at genome-wide level.

The present invention will be described in detail with reference to the drawing figures and specific examples below.

Example 1: Genetic Mapping of Phosphorus Acquisition Efficiency and Identification of Candidate Genes The present invention used a set of soybean core collection of phosphorus efficiency (including 274 soybean accessions) to carry out field trials in Boluo, Guangdong (113°50' east longitude, 23°07' north latitude), used complete randomized block design, design (1.5 m² per plot), set up 4 blocks, and conducted phenotyping for phosphorus efficiency.

Determination of phosphorus content: phosphorus content (mg/plant)=phosphorus concentration (mg/g)×plant dry weight (g/plant), in which phosphorus concentration is measured by colorimetry (Murphy and Riley, 1963).

Determination of total root length: in order to obtain a complete plant root system of the plant, use tools such as shovel to measure 40 cm×40 cm square area (centered on the plant) is dug down to the tip of the taproot; The obtained roots were taken to the laboratory, washed with water, scanned with a scanner, and then the total root length (m/plant) was extracted using the image processing software WinRhizo pro (R é gent instruments, Qu é BEC, Canada).

Calculation of phosphorus acquisition efficiency: phosphorus acquisition efficiency (mg/m)=phosphorus content (mg/plant)=total root length (m/plant).

The shoots and roots of soybean plants at seedling stage (1 month after sowing) were fastened in a 105° C. oven for 30 minutes, then dried in a 75° C. oven to constant weight and weighed.

Based on the next-generation sequencing platform (Illumina NovaSeq PE150), the present invention performs whole genome re-sequencing on the above-mentioned soybean core collection, resulting in a total of 13.5 billion reads. DNA extraction, library construction and sequencing were all completed by Novogene Bioinformatics Technology Co., Ltd, China.

The re-sequencing data analysis process is as follows: Quality control of sequencing files were performed using fastp software; Sequencing reads were aligned to the soybean Williams 82 reference genome (http://plants.ensembl.org/info/website/ftp/index.html) using BWA software; Quality control of BAM files was done by Samtools and Qualimap software; SNPs and indel variants were extracted by GATK software, and the generated VCF variant files were subjected to quality control; genotype imputation were done by Beagle software; Snpeff software was used to annotate the variation effects of SNPs and indels.

The present invention performed population structure analysis, principal component analysis and phylogenetic tree construction based on the above genotyping results, and calculated the kinship, identified subpopulation-differentiation genomic regions by veftools, and evaluated degree of genome-wide LD decay by PopLDdecay software. The present invention removed SNPs with minor allele frequency (MAF)<0.05. Integrating phenotypic data, genotypic data, and kinship matrix, the present invention carried out genome-wide association analysis using mixed linear model, and determined the appropriate significance threshold using GEC software.

FIG. 1 shows the genome-wide association analysis results of phosphorus acquisition efficiency in soybean. At the upper left is a quantile-quantile plot, showing the effect of group structure control. At the bottom is the Manhattan plot, the x- and y-values correspond to the physical locations of SNP and the negative logarithm of P values respectively, the horizontal line in the figure represents the significance threshold of association analysis at genome level. The experimental result indicated that: A significant association signal of phosphorus acquisition efficiency was identified on chromosome 20 (see FIG. 1), and there were 10 candidate genes in the corresponding interval of the signal. According to the expression profile information of these genes in multiple tissues, a gene specifically expressed in the root was focused as a candidate gene, named CPU1. The annotation information showed that CPU1 encodes a SEC12-like protein (guanine nucleotide exchange factor like protein).

Example 2. Cloning and Functional Verification of CPU1

A pair of specific primers F1/RI was designed according to the cDNA sequence of CPU1 gene (as shown in SEQ ID NO: 2), and a 147 bp fragment was amplified using the cDNA samples of the wild-type soybean variety YC04-5 root as templates. A forward Fragment was obtained by using Swa I+Asc I enzyme digestion of the above 147 bp fragment, and was clone into pFGC5941 vector between Swa I and Asc I. The above 147 bp fragment was digested with Sma I+BamH I to obtain a reverse fragment, and then the reverse fragment was cloned into pFGC5941 vector containing the forward fragment between Sma I and BamH I to obtain the recombinant vector. The recombinant vector was transformed into *Agrobacterium tumefaciens* EHA105, and the strain was shaken for standby. The CPU1-RNAi material was obtained by *Agrobacterium tumefaciens*-mediated cotyledon node transformation (Wang et al. 2009), and finally three independent transgenic RNAi lines with significantly lower CPU1 expressions than wild-type plants (RNAi1, RNAi2, RNAi3) were obtained.

The sequences of primers used to amplify the fragment are as follows:

F1:

(SEQ ID NO: 6)
5'-TCAACCCGGGGGCGCGCCATGCTCTCATTTTCGTCTCTG-3';

R1:

(SEQ ID NO: 7)
5'-TGCCGGATCCATTTAAATCGAAAGAGTTCGAAAATTG-3'.

CPU1-RNAi material and wild-type material (YC04-5) were planted in vermiculite in the growth chamber with daily nutrient solution.

The formulation of the nutrient solution is shown in Table 1.

TABLE 1

| Chemical compound | Molecular weight (g/mol) | Concentration of storage solution 1000 × (mmol/L) | Applied concentration 1 × (mmol/L) | Content of storage solution 1000 × (g/L) |
|---|---|---|---|---|
| Stock 1 | | | | |
| $KNO_3$ | 101.1 | 1500 | 1.5 | 151.65 |
| $Ca(NO_3)_2 \cdot 4H_2O$ | 236.15 | 1200 | 1.2 | 283.38 |
| $NH_4NO_3$ | 80.04 | 400 | 0.4 | 32.02 |
| $MgCl_2$ | 203.31 | 25 | 0.025 | 5.08 |
| Stock 2 | | | | |
| Fe-EDTA(Na) | 367.1 | 40 | 0.04 | 14.68 |
| Stock 3 | | | | |
| $(NH_4)_2SO_4$ | 132.4 | 300 | 0.3 | 39.72 |
| Stock 4 | | | | |
| $MgSO_4 \cdot 7H_2O$ | 246.48 | 500 | 0.5 | 123.24 |
| $K_2SO_4$ | 174.27 | 500 | 0.5 | 87.14 |
| $MnSO_4 \cdot H_2O$ | 169.01 | 1.5 | $1.5 \times 10^{-3}$ | 0.25 |
| $ZnSO_4 \cdot 7H_2O$ | 287.55 | 1.5 | $1.5 \times 10^{-3}$ | 0.43 |
| $CuSO_4 \cdot 5H_2O$ | 249.71 | 0.5 | $0.5 \times 10^{-3}$ | 0.13 |
| $(NH_4)_6Mo_7O_{24} \cdot 4H_2O$ | 1235.86 | 0.16 | $0.15 \times 10^{-3}$ | 0.2 |
| $NaB_4O_7 \cdot 10H_2O$ | 381.37 | 2.5 | $2.5 \times 10^{-3}$ | 0.95 |
| Stock 5 | | | | |
| $KH_2PO_4$ | 136.09 | 500 | 0.5 | 68.05 |
| Stock 6 | | | | |
| $CaCl_2$ | 110.98 | 1200 | 1.2 | 133.18 |

The growth conditions are as follows: 13 hours/26° C. light and 11 hours/24° C. dark; light intensity: 400 μmol photons $m^{-2}$ $s^{-1}$; relative humidity: 65%.

18 days after sowing, the shoots and roots of plants were harvested and the roots were scanned. The scanned images were analyzed by WinRHIZO software to obtain the total root length of the plants. The shoots and roots of the plants were dried in an oven at 65° C. for two days and then the dry weight was weighed. The dried plant samples were put into the digestion tube, and 3 ml concentrated nitric acid was added to the digestion furnace for sample digestion. The phosphorus concentration was measured by ICP-MS (Agilent 7900, Agilent Technologies, SantaClara, CA, USA) and the phosphorus acquisition efficiency was calculated.

FIG. 2A-2H show the effects of CPU1 on phosphorus acquisition efficiency, biomass and yield of soybean transgenic plants. FIG. 2A shows the relative expression levels of CPU1 in three independent transgenic RNAi lines; FIG. 2B shows the growth at seedling stage of RNAi lines and wild-type plants; FIG. 2C shows the biomass at seedling stage of RNAi lines and wild-type plants: FIG. 2D shows the plant's phosphorus content at seedling stage of RNAi lines and wild-type plants, FIG. 2E shows the total root length at seedling stage of RNAi lines and wild-type plants; FIG. 2F shows the phosphorus acquisition efficiency at seedling stage of RNAi lines and wild-type plants; FIG. 2G shows the growth at maturity of RNAi lines and wild-type plants; FIG. 2H shows the number of pods per plant at maturity stage of RNAi lines and wild-type plants; * indicates 0.01<P≤0.05 and the difference is significant;  indicates 0.001<P≤0.01 and the significance of the difference is between significant and extremely significant; * indicates P≤0.001 and the difference is extremely significant.

Results are summarized as follows: at seedling stage, phosphorus acquisition efficiency of CPU-RNAi materials was significantly lower than that of wild-type materials (see FIG. 2F), resulting in a significant decrease in plant phosphorus acquisition and biomass of RNAi materials (see FIGS. 2C-2D), but no significant difference in the total root length (see FIG. 2E); at maturity, the yield of CPU1-RNAi materials was significantly lower than that of wild-type materials (see FIGS. 2G-2H). The above results indicate that CPU1 promotes the phosphorus acquisition of plants by improving the phosphorus acquisition efficiency of soybeans rather than the length of roots.

Example 3: Variation of Amino Acid Sequence and Expression Levels of CPU1

CPU1 was identified by genome-wide association studies, indicating that there was sequence variation leading to phenotypic variation in phosphorus acquisition efficiency of soybean population. Therefore, exploring the causal variants will provide valuable information for later gene editing breeding and precise molecular marker assisted selection breeding.

Based on the re-sequencing results and genome-wide association analysis results in Example 1, the inventors found that there were mainly two kinds of CPU1 alleles in the natural soybean population: CPU1-H1 (nucleotide sequence is shown in SEQ ID NO: 5) and CPU1-H2 (nucleotide sequence is shown in SEQ ID NO: 1); the variants significantly associated with phosphorus acquisition efficiency were located in the promoter region and the 5'UTR, and no association signals were found in the coding region, which suggested that the variation in phosphorus acquisition efficiency was not caused by variants in coding regions. In order to determine the causal variants, five soybean accessions of each CPU1-haplotype were randomly selected. The CDS sequences of these 10 soybean accessions were amplified by primers F10/R10 and sequenced, and the expression levels of CPU1 in the roots of these 10 accessions were determined (18 days after sowing).

The extraction and reverse transcription of plant total RNA are as follows: total RNA was extracted according to the instructions of Trizol (Takara, Japan); the first-strand of cDNA was synthesized according to the method described in the One Step gDNA Removal and cDNA Synthesis Supermix Reverse Transcriptase Kit (Transgen, China).

Primers used to amplify CDs sequences were as follows:

```
F10:
                                    (SEQ ID NO: 8)
5'-CGAGGCTCAGCAGGAGAATTCATGGGGAATGATGCAGGGTC-3',

R10:
                                    (SEQ ID NO: 9)
5'-GCCCTTGCTCACCATCATATCTACTGGCCCCCAAA-3'.
```

Gene expression determined by real-time fluorescent quantitative PCR is as follows: real-time fluorescent quantitative PCR analysis was done by using Top Green qPCR SuperMix Kit (TransGen, China).

10 μL reaction system is as follows:

| 2 × Top Mix | 5 μL |
| ddH₂O | 2.2 μL |
| Primer(5 μM) | 0.4 μL each |
| 10-fold diluted cDNA template | 2 μL |

Reaction procedure is as follows: 95° C., 2 min; 95° C., 15 sec; 60° C., 15 sec; 72° C., 30 sec; number of cycles: 40; Using the $2^{-\Delta\Delta Ct}$ method, the relative expression levels of genes were calculated using the soybean housekeeping gene GmEF-la as a reference.

Real time fluorescent quantitative PCR primers are as follows:

```
CPU1-F:
                                    (SEQ ID NO: 10)
5'-TGGAAAAAGAAGCGAACTGGGT-3';

CPU1-R:
                                    (SEQ ID NO: 11)
5'-GCTTCCAACACATAAGTGGTCA-3';

GmEF-1α-F:
                                    (SEQ ID NO: 12)
5'-TGCAAAGGAGGCTGCTAACT-3';

GmEF-1α-R:
                                    (SEQ ID NO: 13)
5'-CAGCATCACCGTTCTTCAAA-3'.
```

Figure 3:
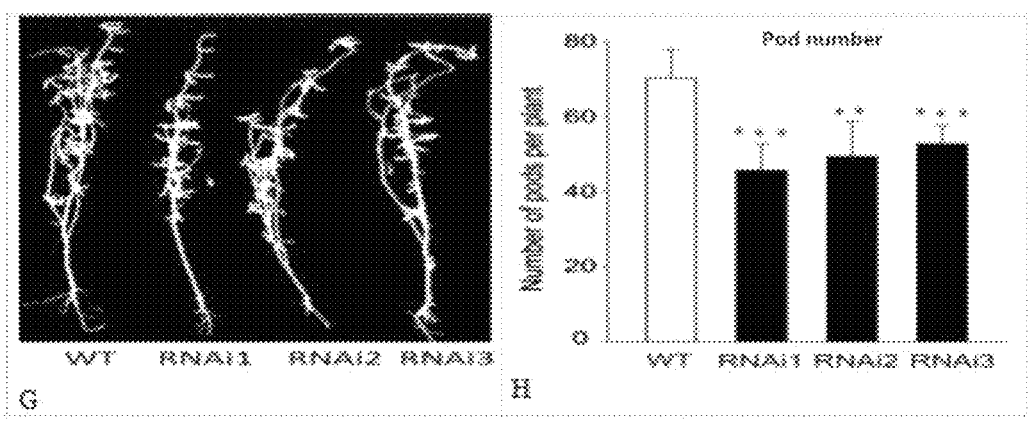
FIG. 3. Comparison of amino acid sequences between two alleles of CPU1. The 360 residue amino acid sequence is shown in SEQ ID NO: 27.

FIG. 3 shows the comparison of amino acid sequences between two CPU1 alleles, and each allele group contains five randomly selected soybean accessions. FIG. 4 shows the comparison of the expression levels between the two CPU1 alleles, and the 10 soybean accessions are the same as those used in FIG. 3. Results are summarized as follows: there was no difference in amino acid sequence between the two alleles (see FIG. 3; the 360 residue amino acid sequence is shown in SEQ ID NO: 27), there was no difference in expression levels between the two alleles (see FIG. 4); therefore, the CPU1 variation was attributed to neither the difference of amino acid sequence nor expression levels, indicating that the causal variants was neither in the coding region norin the promoter region.

Example 4: Determination of the Location of CPU1 Causal Variants

Based on the genome-wide association analysis results mentioned above, there were two SNPs between the two alleles of CPU1 at 5'UTR. In order to determine whether 5'UTR is the area where causal variants is located, the inventors constructed six recombinant vectors (reassembling promoters and 5'UTR from different alleles (H1 or H2) of CPU1, and ligating them to CPU1-GFP), transformed them into soybean hairy roots, and quantified the protein levels through Western Blot. In Western Blot, primary antibody anti-GFP antibody (1:1,000; TransGen, Beijing, China) or anti H+-ATPase (1:2,000; Agrisera, Vännäs, Sweden) was added and incubated overnight; then the corresponding secondary antibody horseradish peroxidase (HRP)-conjugated anti-mouse IgG (TransGen, Beijing, China) or horseradish peroxidase (HRP)-conjugated anti-rabbit IgG (Biosharp, Hefei, China) was added; the SuperSignal West Dura Trial Kit (Thermo Scientific, MA, USA) was used for exposure development and the Amersham Imager 600 System (GE Healthcare Bio-Sciences AB, Uppsala, Sweden) was used for imaging analysis.

Construction of recombinant vector is as follows:
(1) The CDS of CPU1 (as shown in SEQ ID NO: 4) was amplified using primers F10/R10, and cloned into the EcoRI and AseI restriction sites of pFGC5941-p35S-GFP vector to form CPU1-GFP;
(2) Primers F11/R11 were used to amplify the promoter-5'UTR of H1 and H2 alleles respectively, and then cloned into the EcoRI digestion site of CPU1-GFP vector to form $H2_{promoter}+H2_{5'UTR}$:CPU1-GFP (vector A in FIG. 5A) and $H1_{promoter}H1_{5'UTR}$:CPU1-GFP (vector B in FIG. 5A);
(3) The promoter region and 5'UTR of two alleles were amplified using primers F11/R12 and F12/R11 respectively. The promoter region and 5'UTR primers F11/R11 were connected by overlapping PCR to form PCR products of $H2_{promoter}+H1_{5'UTR}$ and $H1_{promoter}+H2_{5'UTR}$. These two PCR products were cloned into the EcoRI digestion site of CPU1-GFP vector in (2) respectively to form $H2_{promoter}+H1_{5'UTR}$:CPU1-GFP (vector C in FIG. 5A) and $H1_{promoter}+H2_{5'UTR}$:CPU1-GFP (vector D in FIG. 5B);
(4) Primers F13/R11 were used to amplify the 5'UTR of the two alleles, and then cloned into the EcoRI digestion site of CPU1-GFP vector in (2) to form $H2_{5'UTR}$:CPU1-GFP (vector E in FIG. 5A) and $H1_{5'UTR}$:CPU1-GFP (vector f in FIG. 5A).

Primers used to construct the recombinant vector are as follows:

```
F10:
                              (SEQ ID NO: 8)
5'-CGAGGCTCAGCAGGAGAATTCATGGGGAATGATGCAGGGTC-3'

F11:
                             (SEQ ID NO: 14)
5'-CGAGGCTCAGCAGGAGGCGCGCCGGACATGTGCACCACGAGGAATAT

TAGG-3'

F12:
                             (SEQ ID NO: 15)
5'-TCGCGCTAATGCCGCGGAATCTTAAGCG-3'

F13:
                             (SEQ ID NO: 16)
5'-CGAGGCTCAGCAGGAGAATTCCGGAATCTTAAGCGAATATC-3'

R10:
                              (SEQ ID NO: 9)
5'-GCCCTTGCTCACCATCATATCTACTGGCCCCCAAA-3'
```

```
-continued
R11:
                             (SEQ ID NO: 17)
5'-TGCATCATTCCCCATCGAAAGTGTTCGAAAATTGGATAC CCAG-3'

R12:
                             (SEQ ID NO: 18)
5'-CGCTTAAGATTCCGCGGCATTAGCGCGA-3'
```

FIGS. 5A-5B show the region of the causal variants of CPU1 determined by the construction of recombinant vector and Western-blot. FIG. 5A shows the recombinant vectors of promoter and 5'UTR from different CPU1 alleles. FIG. 5B shows the Western-blot results of soybean hairy roots containing the six recombinant vectors in 5A. In multiple comparisons, different English letters represent significant differences ($P<0.05$).

Results were summarized as follows: Only 5'UTR cannot initiate the expression of CPU1-GFP; The promoters of different alleles failed to change the protein abundance of CPU1-GFP, indicating that the causal variants were not in the promoter region; The 5'UTRs of different alleles significantly changed the protein abundance of CPU1-GFP, indicating that the causal variants were located in the 5'UTR, which affected the translation efficiency of CPU1.

Example 5: Identification of the Causal Variants of CPU1

There were two SNPs in the 5'UTR. The inventors found that there was an upstream open reading frame (uORF) in the 5'UTR of CPU1, and the two SNPs were located in this uORF, at the 20th bp (the genotype is A in the phosphorus efficient allele CPU1-H2; G in the phosphorus inefficient allele CPU1-H1) and 83rd bp (the genotype is C in the phosphorus efficient allele CPU1-H2; A in the phosphorus inefficient allele CPU1-H1) of the uORF, resulting in amino acid changes and premature termination, respectively.

In order to determine the causal variant and whether it affected the translation efficiency of CPU1 dependently on uORF, the inventors constructed 6 recombinant vectors (different genotypes of two SNPs were reassembled; the starting codon of uORF was artificially mutated as ATG→AAA; Then ligated to CPU1-GFP), transformed them into soybean hairy roots, and quantified the level of CPU1-GFP protein by Western-blot. In Western-blot, primary antibody anti-GFP antibody (1:1,000; TransGen, Beijing, China) or anti H+-ATPase (1:2,000; Agrisera, Vännäs, Sweden) was added and incubated overnight, then the corresponding secondary antibody horseradish peroxidase (HRP)-conjugated anti-mouse IgG (TransGen, Beijing, China) or horseradish peroxidase (HRP)-conjugated anti-rabbit IgG (Biosharp, Hefei, China) was added; the SuperSignal West Dura Trial Kit (Thermo Scientific, MA, USA) was used for exposure development and the Amersham Imager 600 System (GE Healthcare Bio-Sciences AB, Uppsala, Sweden) was used for imaging analysis.

Construction of recombinant vector is as follows:
(1) The CDs sequence of CPU1 was amplified with primerS F14/R10, and then cloned into the AscI digestion site of pFGC5941-p35s-GFP to generate the p35s:CPU1-GFP recombinant vector;
(2) The 5'UTRs of the two alleles were amplified with primers F15/R15;
(3) The 5'UTR of $H1_{SNP476}+H2_{SNP413}$ genotype was obtained by overlapping PCR with primers F16/F17/R15;

(4) The 5'UTR of H2$_{SMP476}$+H1$_{SNP413}$ genotype was obtained by overlapping PCR with primers F15/F18/R15;

(5) The 5'UTR of two alleles with the mutated initial codon mutation (ATG→AAA) were amplified by primers F19/R15;

(6) The six PCR products in (2)-(5) were cloned into the AscI site of p35S:CPU1-GFP vector in (1) respectively, and the G-L recombinant vectors in FIG. 6A were constructed.

Primers used to construct the recombinant vector are as follows:

F14:
(SEQ ID NO: 19)
5'-TTACAATTACCATGGGGCGCGCCATGGGGAATGATGCAGGGTC-3'

F15:
(SEQ ID NO: 20)
5'-TTACAATTACCATGGCGGAATCTTAAGCGAATATC-3'

F16:
(SEQ ID NO: 21)
5'-TTACAATTACCATGGCGGAATCTTAAGCGAATATCTCCATAGTTGCT

AAT-3'

F17:
(SEQ ID NO: 22)
5'-ATATCTCCATAGTTGCTAATATGTTTTGTTTCTTCCAGCGTTGTT-3'

F18:
(SEQ ID NO: 23)
5'-CTTCAATTTTTTAAACCCTCAAAAT-3'

F19:
(SEQ ID NO: 24)
5'-TTACAATTACCATGGCGGAATCTTAAGCGAATATCTCCATAGTTGCT

AATAAATTTTG-3'

R10:
(SEQ ID NO: 9)
5'-GCCCTTGCTCACCATCATATCTACTGGCCCCCAAA-3'

R15:
(SEQ ID NO: 25)
5'-TGCATCATTCCCCATCGAAAGTGTTCGAAAATT-3'

R18:
(SEQ ID NO: 26)
5'-ATTTTGAGGGTTTAAAAAATTGAAG-3'

FIGS. 6A-6B show CPU1 causal variants identified by recombinant vector construction and Western-blot. FIG. 6A shows recombinant vectors containing 5'UTR of different genotypes for the two SNP sites. FIG. 6B shows Western-blot results of soybean hairy roots containing the six recombinant vectors in FIG. 6A. In multiple comparisons, different English letters represent significant differences (P<0.05).

Results were summarized as follows: (1) Without mutation of uORF start codon, SNP413 leading to premature termination significantly changed the translation efficiency of CPU1-GFP, whereas SNP476 causing amino acid changes had no significant effect on translation efficiency;

(2) When the starting codon of uORF is mutated, no CPU1-GFP protein could be detected, indicating that the uORF was necessary for the translation of CPU1-GFP. Most reports have reported that uORF inhibits the translation of downstream genes. The inventor discovered that uORF can also promote the translation of downstream genes in plants, and the invention is the first report that the natural variation of uORF underlies phenotypic variation in plant populations.

To sum up, the present invention identified a SEC12-like protein gene CPU1 by genome-wide association studies, and verified the function of the gene in phosphorus acquisition efficiency. In nature, the gene CPU1 has two major alleles, and its 5'UTR has a uORF that promotes the translation of CPU1. One SNP in the uORF of phosphorus-inefficient allele CPU1-H1 leads to the extension of uORF length, improves the translation efficiency of CPU1, and forms the phosphorus-efficient allele CPU1-H2, which would accelerate the molecular breeding for phosphorus efficiency, and the identified causal variants will provide a precise target for gene editing. In a word, the present invention has theoretical and practical significance for enhancing phosphorus efficiency and yield in crops and developing resource-saving and environment-friendly ecological agriculture.

It should be noted that the examples mentioned above do not limit the present invention in any form, and all technical solutions obtained by equivalent replacement or equivalent transformation fall within the protection scope of the present invention.

References are as follows:

Shi Hui, Wang Siming. Shift of Status: Comparative Study on the Development of Soybean in China and the United States. Agricultural History in China (2018). 37(5):58-64.

Li Xinxin, Xu Ruineng, Liao Hong. Contributions of Symbiotic Nitrogen Fixation in Soybean to Reducing Fertilization While Increasing Efficiency in Agriculture. Soybean Science. (2016). 35(4):531-535.

Yu, J., and Buckler, E. S. Genetic Association Mapping and Genome Organization of Maize. Current Opinion in Biotechnology. (2006). 17(2):155-160.

Schmutz, J., Cannon, S. B., Schlueter, J. et al. Genome Sequence of the Palaeopolyploid Soybean. Nature. (2010). 463(7278):178-183.

Lam, H. M., Xu, X., Liu, X. et al. Resequencing of 31 Wild and Cultivated Soybean Genomes Identifies Patterns of Genetic Diversity and Selection. Nature Genetics. (2010). 42(12):1053-1059.

Zhou, Z., Jiang, Y., Wang, Z. et al. Resequencing 302 Wild and Cultivated Accessions Identifies Genes Related to Domestication and Improvement in Soybean. Nature biotechnology. (2015). 33(4):408-414.

Fang, C., Ma, Y., Wu, S. et al. Genome-wide Association Studies Dissect the Genetic Networks Underlying Agronomical Traits in Soybean. Genome Biology. (2017). 18.

Wang, X., Wang, Y., Tian, J. et al. Overexpressing AtPAP15 Enhances Phosphorus Efficiency in Soybean. Plant Physiol. (2009) 151, 233-240.

Sequence Listing Information:
DTD Version: V1_3
File Name: SEQUENCE LISTING.xml
Software Name: WIPO Sequence
Software Version: 2.1.0
Production Date: 2022 Oct. 12
General Information:
Current application/IP Office: CN Current application/Application number: 2021112450606
Current application/Filing date: 2021 Oct. 26
Earliest priority application/IP Office: CN
Earliest priority application/Application number: 2021112450606
Earliest priority application/Filing date: 2021 Oct. 26
Applicant name: Fujian Agriculture and Forestry University
Applicant name/Language: en
Inventor name: Guo Zilong
Inventor name/Language: en
Invention title: Sec 12-like protein gene CPUI and application thereof in
improving soybean phosphorus efficiency ( en )
Sequence Total Quantity: 26
Sequences:
Sequence Number (ID): 1
Length: 6238
Molecule Type: DNA
Features Location/Qualifiers:
source, 1 . . . 6238
mol_type, genomic DNA
organism, Glycine max
Residues:

```
cggaatctta agcgaatatc tccatagttg ctaatatgtt ttgtttcttc cagcattgtt   60
gcatttactg gacccatctc tcccttcttt ctattaaaca aatcgcttca attttttcaa  120
ccctcaaaat taatcaactt tcattttttt tataaatcca acccctaaa catattttca  180
cattgcgttc aagcaacagt tgcatcatcc taataaaacc ctgtgatcat atacattcat  240
actcagcaac cttaaaacac aatatcacgt aaaaaggtg agacatgtct ttttcgaacg  300
cgtgacatta attaataagg ctgtgccttg tttcattggt taattaatta atgattaaat  360
aaagcaaggc aaagctcttt ctatcttcct ttgacttttt ttttcagagg ctctattttt  420
cttctctgac atttctattt aaatttgccg aagaatccaa ttcaccgatc tccgaagagc  480
tccatttgga aaaagaagcg aactgggtat ccaattttcg aacactttcg atggggaatg  540
atgcagggtc acctcagggt ccggttacgt gtgggtcgtg gattcggagg cctgagaatt  600
tgaacttggt ggtgttagga aggtccagac gtggcaattc ttgtccttct ctcttggaga  660
ttttctcctt cgatcccaag accacttctc tgtctacctg tcctctggta ttcctctaaa  720
actctgaata tacatacacg tatcatgtgt gtgtgtgtta tgtttaagta tgcatgtgcg  780
tgtgtaattt attttatatt atgtatagag tgactcattt gtaacattaa tttgttttgt  840
gcagaccctt tttattgtat gttgaaaaac tgttgttttc tttgtgttat gtttgtgtat  900
gtctgagcat gtagattctg tggagtgagt catttgaaac acgagccttt ttgtgcatat  960
acttttgat tattggccga gaaactgttt actttttcct ctctgaagca gatggtgggt 1020
ggaagtagat attatgcaca aattctgttg ttgaaaagta tttttagtgt tgaaattctg 1080
ggttgctgaa tggaagcaaa gtttgaatgg gctatggctt tggtttaat gatgtttttg 1140
ttttgatatt tcagaccact tatgtgttgg aagcagagga aggtgatcct gttgctattg 1200
cagtccaccc aagtgggggat gattttgtgt gcgctctcag caatggtagc tgcaagtaag 1260
tttcttttgt aagggcttcg agattgaagc gttcttttat atgtattcat cttttgaaat 1320
acttccgtga tgtgtctcaa cttgcatttc taaaattagc agttcacttg cgataatctc 1380
agaaacagac tccaacattt tatctttctt taaccgttca aagtacaaga taaaactgta 1440
ggctcagttc taccaaattt ctctctgaca gtttctcgtt cctttttttt ttttccctga 1500
gaactaggga atgtttgaca taatagttat tgttgtttct taggtataga tagatgaatt 1560
ttgccttgag ttattttcgt tggatgattt gtgccatcct tggatagtta agatcctaca 1620
cnatcagtta ggtatatggc aatagcttta gaggtagagt tagactcatt tcattctcaa 1680
ttctaatatg atatcaaagc gtattcaggc ctgatgtttg accacctgca catgtctggt 1740
gcagcctaca aacttcatgc tctagcctct agatgtctag tcctggacat gatatcctcc 1800
catgattctt attctaatt gatactgaac tgaacatata atatagattg aagtatttct 1860
ccatggcttg tagattgttt gagctgtatg gtcgtgaaac aaacatgaag ttgttggcta 1920
aggaactggc tcctctacag ggtattggtc ctcagaaatg cattgctttt agtgttgatg 1980
ggtctaaatt tgctgctggt gggttggtaa gcatcacttt atatccaacc aattgctttt 2040
attttctatt cagcactttg agtttttcct tttcaagttt gatcttgtat gtttgacttc 2100
tgtctttaac aagtgtagga tggacatctc agaattatgg agtggcctag tatgcgcgtg 2160
attttggatg aaccaagagc acacaaatca gttcgggata tggattttag gtaggtatag 2220
taaacaaatc tatttggatc cttctaaagg aggcatcaat ccctacagct agtaaaattg 2280
taataaatag ttgataaagt tggttactat agtaatgtta tttcgagttc ttacaaccag 2340
ataagataat ttttgctttg catgttcatg cctgcaataa cttgactgtg tagatatgat 2400
cttttagaaa ataaaagtat gttacattgt aaatatttta atcctgaaac tttaatgata 2460
ttgtacttac tatattgtcc ttcatttttt cccttacttt agtctagact cagaatttct 2520
agcttcaact tctactgatg gttcagcaag aatctggaag attgaagatg gtgttccttt 2580
gactactttg tctcgcaact cggtatggtg tatttgattt aagaacctgg ggcaagatct 2640
gtatgcagta cttgtattgc ttgatccaaa tatttccttt tgtctcttta ggatgaaaag 2700
attgaattat gtcgattttc catggatgga accaaaccat ttttattttg ctctgttcaa 2760
aaaggtataa gagtatcttg tttctagtat attctatagt attaatttgt atattcttca 2820
aatctctttg accagcaaag catggccttt ataatagata cttatatctt ttagcaggtg 2880
atacttctgt cactgcggtt tatgagatta gcacatggaa taaaattggg cacaagaggc 2940
tgattagaaa gtctgcttca gtaatgtcca ttagccatga tgggaaatac ctttctctgt 3000
aagaacctgc agttatcttc tgactttttg cttatgtgt ggtcattggt caacattctt 3060
cctttatctt tcgttagttt tgatttccaa attttatcca gatagttttg tgactattgt 3120
aagtcttgca tcttaagcaa gtgaataatt tagaattttt atttcttttg ttttgaccaa 3180
tagaattttt attcaattgc cttctgttat cctcagcagt ctgcatgctt gaaggagtgc 3240
ttgaatcccc ctcccccatg cattatctga tgtaggaatg taaatatccc aatctaaaaa 3300
tgttgaccag gaggtctttc gtttacctga cttctcccct gggtaaacaa acatctccat 3360
cataatcgaa actaaaactt caatataaga gtggaagaga ttgaatagag ctgaaattg 3420
cattcttcaa tgaataccta agtgtaaaaa agtttaatta agtctctttg aaaattgaaa 3480
```

-continued

```
tgtactctta ccataaattt cagatttccg tgtaagtcct tcttattaat aaagccattc 3540
actttcttaa ctgtcataga tctccttgtc tgtattaata tataaatcat ttgggtacca 3600
aagtgggatt gtgattttgg ccatttctcc aaaattgtga atgaatgaag aaaacaatgt 3660
tagaattgat catgttttc catcttatta ctttggctct ttttgatcta tagcactaca 3720
tttatgttta tgtggctcta gttccttctt tgagtgtctt ttcttgtgaa tcatttttg 3780
acctttgcac acataagtca tctgggtgat agactaccta atcattttct tctgcataac 3840
tgcagagttt tttagtttgt gtttactgta tctccaattt aatgcataaa aaagctgttg 3900
aaaagttgac tgcagaatgc acataaatta acttgtttaa actcattttg tccgtcagct 3960
cgacnatcct atttccttt agatctgcat aactgcaggg tttttagtt tgtgtatttt 4020
actgtatctc caatttaatg cattttagct gttgaaaagt tgactgcagc acataaatta 4080
acttgtttaa actcattttg tctgtcagct tgatcctatt tccttttaga atcataaag 4140
ccccaaaact catgactgta atgcatttcc caggaaacag cataacctaa aataacatat 4200
cttattctgt ttttcttcaa ttgtagcttg ccactaggca tggacaccta ttggggggg 4260
ggggggggat gtctaatttt taataattaa taattttaaa aaatatttat ttttacacat 4320
aaaattgaaa ctaattttta ttttaaatga taataacttt aatcattatc ataaaaacaa 4380
caaacacaaa ttagttttc acaattttat tcaagtaatc accttaacca ttacagtaat 4440
aataacaagc acaactaatt ttatataatt ttacactaac taactttaat cattattata 4500
ataataacat agataattcg tttttaatag ttttaaatta accaacttaa aaatatatat 4560
ctatgtacat gagaagtgcc aagggagggg gggggtagct gttaaagtaa gtcatagctt 4620
gtttaattat aactataaaa aaatgtttaa atatgttgtg gtgaagtaac tatagcacac 4680
ttgtaaacca tattagcgga gtctgggta catcctctat aaaattacta taatatattc 4740
accaaacaaa ttactaaaat attttgatta aaacatttga aggcctgtaa taagttcgtg 4800
atctgatttg cacttcactt gtatatcaca taacaatcta tgataatatg tccccagcat 4860
ttcttctgct catcggactt ctgtaatttc aggggcagta aagatggaga catatgtgta 4920
gttgaagtaa agaaaatgca gatataccat tatagcaaga gattgcacct gggtacaaat 4980
attgcatatc tggagttctg tcccgggggaa aggtaatttc tatgctctat tggtttaatt 5040
tggcacctct gataaaatatc aatgtatgca gaattttagt aattgctgaa acctcctcct 5100
ttttgaatat tggacacagt tgggattaag ctattcattt gaatattgga acatgcattg 5160
ggtacaaaac cttggtgtta gcaatgaatt tatattagca attgattttt tctcatcaga 5220
tcattagcca gagtaaatgt ggattttga aattgaacct tgtgttaga gaaccaatct 5280
gacctgaaag cttaagtcat ttataatgga agttaagtcg tttttttaa taaattatag 5340
ctaacatgcc tctgcagatt accttttagt attggattct gattctgtga tcatacatag 5400
taatttctca ttttaaaaaa aatacattca gttaataaat ctattctttt ggtcttgcct 5460
actcacccag gctttttttg ttcagggttt tacttacaac ctcagtagaa tggggagcgc 5520
tggtcaccaa gctgactgta cctaaagatt ggaaaggttc tctctctctt acacgcacac 5580
acttgcatgc atcccttctt cattctaacg ccttacaata atgtctattc aatttgacat 5640
tttcaatatc ctttcaaacc tgcagagtgg cagatctatt tggtgctatt gggactattt 5700
ttagcatcag ctgttgcatt ttacatattc tttgagaact ctgattcatt ctggaacttt 5760
cccatgggca aagaccaacc agcaagacca aggtttaaac ctgtgttaaa agatccccag 5820
tcttatgatg accaaaatat ttgggggcca gtagatatgt gatcacatta acattcttga 5880
tttagtcttc ggtgctgttt tggaagcagt atcagtagct gtaactggta tcaatattta 5940
tttaagccct tatagagtta ggcacttgac tggtattaca aacatttact tctatttttt 6000
tggggtgaaa attctgagcc aaaggccatg attggtatgt aattttaata gaaactttag 6060
gaataatcaa atagcttcct taaatttaca agttacacgc aaggctgctt tgtagctatg 6120
tgatgggatc cattgaagag gcacgtcttt ggatatcttt ccatttttct tattttgttt 6180
cttgttttaa tgataacctc ttacattggt tttatgcctt tggttagaga aaaataaa   6238
```

Sequence Number (ID): 2
Length: 1915
Molecule Type: DNA
Features Location/Qualifiers:
source, 1 . . . 1915
mol_type, genomic DNA
organism, Glycine max
Residues:

```
cggaatctta agcgaatatc tccatagttg ctaatatgtt ttgtttcttc cagcattgtt   60
gcatttactg gacccatctc tcccttcttt ctattaaaca aatcgcttca attttttcaa  120
ccctcaaaat taatcaactt tcattttttt tataaatcca acccctaaa catatttca  180
cattgcgttc aagcaacagt tgcatcatcc taataaaacc ctgtgatcat atacattcat  240
actcagcaac cttaaaacac aatatcacgt aaaaaagaat ccaattcacc gatctccgaa  300
gagctccatt tggaaaaaga agcgaactgg gtatccaatt ttcgaacact ttcgatgggg  360
aatgatgcag ggtcacctca gggtccggtt acgtgtgggt cgtggattcg gaggcctgag  420
aatttgaact tggtggtgtt aggaaggtcc agacgtggca attcttgtcc ttctctcttg  480
gagatttct ccttcgatcc caagaccact tctctgtcta cctgtcctct gaccacttat  540
gtgttggaag cagaggaagg tgatcctgtt gctattgcag tccacccaag tggggatgat  600
tttgtgtgcg ctctcagcaa tggtagctgc aaattgtttg agctgtatgg tcgtgaaaca  660
aacatgaagt tgttggctaa ggaactggct cctctacagg gtattggtcc tcagaaatgc  720
attgcttta gtgttgatgg gtctaaattt gctgctggtg ggttggatgg acatctcaga  780
attatggagt ggcctagtat gcgcgtgatt ttggatgaac caagagcaca caaatcagtt  840
cgggatatgg attttagtct agactcagaa tttctagctt caacttctac tgatggttca  900
gcaagaatct ggaagattga agatggtgtt cctttgacta ctttgtctcg caactcggat  960
gaaaagattg aattatgtcg attttccatg gatggaacca aaccatttt attttgctct 1020
gttcaaaaag gtgatacttc tgtcactgcg gtttatgaga ttagcacatg gaataaaatt 1080
gggcacaaga ggctgattag aaagtctgct tcagtaatgt ccattagcca tgatgggaaa 1140
tacctttctc tgggcagtaa agatggagac atatgtgtag ttgaagtaaa gaaaatgcag 1200
atataccatt atagcaagag attgcacctg ggtacaaata ttgcatatct ggagttctgt 1260
cccgggggaaa gggttttact tacaacctca gtagaatggg gagcgctggt caccaagctg 1320
actgtacctaa aagattggaa agagtggcag atctatttgg tgctattggg actatttta 1380
gcatcagctg ttgcatttta catattcttt gagaactctg attcattctg gaactttccc 1440
```

-continued

```
atgggcaaag accaaccagc aagaccaagg tttaaacctg tgttaaaaga tccccagtct 1500
tatgatgacc aaaatatttg ggggccagta gatatgtgat cacattaaca ttcttgattt 1560
agtcttcggt gctgttttgg aagcagtatc agtagctgta actggtatca atatttattt 1620
aagcccttat agagttaggc acttgactgg tattacaaac atttacttct attttttttgg 1680
ggtgaaaatt ctgagccaaa ggccatgatt ggtatgtaat tttaatagaa actttaggaa 1740
taatcaaata gcttccttaa atttacaagt tacacgcaag gctgctttgt agctatgtga 1800
tgggatccat tgaagaggca cgtctttgga tatctttcca ttttttcttat tttgtttctt 1860
gttttaatga taacctctta cattggtttt atgcctttgg ttagagaaaa ataaa       1915

Sequence Number (ID): 3
Length: 120
Molecule Type: DNA
Features Location/Qualifiers:
source, 1 . . . 120
mol_type, genomic DNA
organism, Glycine max
Residues:
atgtttgtt tcttccagca ttgttgcatt tactggaccc atctctccct tctttctatt   60
aaacaaatcg cttcaatttt ttcaaccctc aaaattaatc aactttcatt ttttttataa  120

Sequence Number (ID): 4
Length: 1185
Molecule Type: DNA
Features Location/Qualifiers:
source, 1 . . . 1185
mol_type, genomic DNA
organism, Glycine max
Residues:
atggggaatg atgcagggtc acctcagggt ccggttacgt gtgggtcgtg gattcggagg   60
cctgagaatt tgaacttggt ggtgttagga aggtccagac gtggcaattc ttgtccttct  120
ctcttggaga ttttctcctt cgatcccaag accacttctc tgtctacctg tcctctgacc  180
acttatgtgt tggaagcaga ggaaggtgat cctgttgcta ttgcagtcca cccaagtggg  240
gatgattttg tgtgcgctct cagcaatggt agctgcaaat tgtttgagct gtatggtcgt  300
gaaacaaaca tgaagttgtt ggctaaggaa ctggctcctc tacagggtat tggtcctcag  360
aaatgcattg cttttagtgt tgatgggtct aaatttgctg ctggtgggtt ggatggacat  420
ctcagaatta tggagtggcc tagtatgcgc gtgattttgg atgaaccaag agcacacaaa  480
tcagttcggg atatggattt tagtctagac tcagaatttc tagcttcaac ttctactgat  540
ggttcagcaa gaatctggaa gattgaagat ggtgttcctt tgactacttt gtctcgcaac  600
tcggatgaaa agattgaatt atgtcgattt tccatggatg gaaccaaacc atttttattt  660
tgctctgttc aaaaaggtga tacttctgtc actgcggttt atgagattag cacatggaat  720
aaaattgggc acaagaggct gattagaaag tctgcttcag taatgtccat tagccatgat  780
gggaaatacc tttctctggg cagtaaagat ggagacatat gtgtagttga agtaaagaaa  840
atgcagatat accattatag caagagattg cacctgggta caaatattgc atatctggag  900
ttctgtcccg gggaaagggt tttacttaca acctcagtag aatggggagc gctggtcacc  960
aagctgactg tacctaaaga ttggaaagag tggcagatct atttggtgct attgggacta 1020
ttttttagcat cagctgttgc attttacata ttctttgaga actctgattc attctggaac 1080
tttcccatgg gcaaagacca accagcaaga ccaaggttta aacctgtgtt aaaagatccc 1140
cagtcttatg atgaccaaaa tatttggggg ccagtagata tgtga             1185

Sequence Number (ID): 5
Length: 6241
Molecule Type: DNA
Features Location/Qualifiers:
source, 1 . . . 6241
mol_type, genomic DNA
organism, Glycine max
Residues:
cggaatctta agcgaatatc tccatagttg ctaatatgtt ttgtttcttc cagcgttgtt   60
gcatttactg gacccatctc tcccttcttt ctattaaaca aatcgcttca attttttaaa  120
ccctcaaaat taatcaactt tcattttttt tataaatcca accccctaaa catattttca  180
cattgcgttc aagcaacagt tgcatcatcc taataaaacc ctgtgatcat atacattcat  240
actcagcaac cttaaaacac aatatcacgt aaaaaaggtg agacatgtct ttttcgaacg  300
cnacgtgaca ttaattaata aggctgtgcc ttgtttcatt ggttaattaa ttaatgatta  360
aataaagcaa ggcaaagctc tttctatctt cctttgactt tttttttcag aggctctatt  420
tttcttctct gacatttcta tttaaatttg ccgaagaatc caattcaccg atctccgaag  480
agctccattt ggaaaaagaa gcgaactggg tatccaattt tcgaacactt tcgatggggga  540
atgatgcagg gtcacctcag ggtccggtta cgtgtgggtc gtggattcgg aggcctgaga  600
atttgaactt ggtggtgtta ggaaggtcca gacgtgctac ctgtcctcct tctctcttgg  660
agattttctc cttcgatccc aagaccactt ctctgtctac ctgtctgtctac gtattcctct  720
aaaactctga atatacatac acgtatcatg tgtgtgtgtg ttgtgtttaa gtatgcatgt  780
gcgtgtgtaa tttatttat attatgtata gagtgactca tttgtaacat taatttgttt  840
tgtgcagacc ctttttattg tatgttgaaa aactgttgtt ttctttgtgt tatgtttgtg  900
tatgtctgag catgtagatt ctgtggagtg agtcatttga aacacgagcc tttttgtgca  960
tatacttttt gattattggc cgagaaactg tttacttttt cctctctgaa gcagatggtg 1020
ggtggaagta gatattatgc acaaattctg ttgttgaaaa gtatttttag tgttgaaatt 1080
ctgggttgct gaatggaagc aaagtttgaa tgggctatgg ctttggtttt aatgatgttt 1140
ttgtttttgat atttcagacc acttatgtgt tggaagcaga ggaaggtgat cctgttgcta 1200
ttgcagtcca cccaagtggg gatgattttg tgtgcgctct cagcaatggt agctgcaagt 1260
aagtttcttt tgtaagggct tcgagattga agcgttcttt tatatgtatt catcttttga 1320
```

-continued

```
aatacttccg tgatgtgtct caacttgcat ttctaaaatt agcagttcac ttgcgataat 1380
ctcagaaaca gactccaaca ttttatcttt ctttaaccgt tcaaagtaca agataaaact 1440
gtaggctcag ttctaccaaa tttctctctg acagtttctc gttccttttt tttttttccc 1500
tgggaactag ggaatgtttg acataatagt tattgttgtt tcttaggtat agatagatga 1560
attttgcctt gagttatttt cgttggatga tttgtgccat ccttggatag ttaagatcct 1620
acatcagtta ggtatatggc aatagcttta gaggtagagt tagactcatt tcattctcaa 1680
ttctaatatg atatcaaagc gtattcaggc ctgatgtttg accacctgca catgtctggt 1740
gcagcctaca aacttcatgc tctagcctct agatgtctag tcctggacat gatatcctcc 1800
catgattctt atttctaatt gatactgaac tgaacatata atatagattg aagtatttct 1860
ccatggcttg tagattgttt gagctgtatg gtcgtgaaac aaacatgaag ttgttggcta 1920
aggaactggc tcctctacag ggtattggtc ctcagaaatg cattgctttt agtgttgatg 1980
ggtctaaatt tgctgctggt gggttggtaa gcatcacttt atatccaacc aattgctttt 2040
attttctatt cagcactttg agtttttcct tttcaagttt gatcttgtat gtttgacttc 2100
tgtctttaac aagtgtagga tggacatctc agaattatgg agtggcctag tatgcgcgtg 2160
attttggatg aaccaagagc acacaaatca gttcgggata tggattttag gtaggtatag 2220
taaacaaatc tatttggatc cttctaaagg aggcatcaat ccctacagct agtaaaattg 2280
taataaatag ttgataaagt tggttactat agtaatgtta tttcgagttc ttacaaccag 2340
ataagataat ttttgctttg catgttcatg cctgcaataa cttgactgtg tagatatgat 2400
cttttagaaa ataaaagtat gttacattgt aaatatttta atcctgaaac tttaatgata 2460
ttgtacttac tatattgtcc ttcatttttt cccttacttt agtctagact cagaatttct 2520
agcttcaact tctactgatg gttcagcaag aatctggaag attgaagatg gtgttccttt 2580
gactactttg tctcgcaact cggtatggtg tatttgattt aagaacctgg ggcaagatct 2640
gtacnatgca gtacttgtat tgcttgatcc aaatatttcc ttttgtctct ttaggatgaa 2700
aagattgaat tatgtcgatt ttccatggat ggaaccaaac cattttattt ttgctctgtt 2760
caaaaaggta taagagtatc ttgtttctag tatattctat agtattaatt tgtatattct 2820
tcaaatctct ttgaccagca aagcatggcc tttataatag atacttatat cttttagcag 2880
gtgatacttc tgtcactgcg gtttatgaga ttagcacatg gaataaaatt gggcacaaga 2940
ggctgattag aaagtctgct tcagtaatgt ccattagcca tgatgggaaa tacctttctc 3000
tgtaagaacc tgcagttatc ttctgacttt ttggcttatg tgtggtcatt ggtcaacatt 3060
cttcctttat ctttcgttag ttttgatttc caaattttat ccagatagtt ttgtgactat 3120
tgtaagtctt gcatcttaag caagtgaata atttagaatt tttatttctt ttgtttttgac 3180
caatagaatt tttattcaat tgccttctgt tatcctcagc agtctgcatg cttgaaggag 3240
tgcttgaatc cccctccccc atgcattatc tgatgtagga atgtaaatat cccaatctaa 3300
aaatgttgac caggaggtct ttcgtttacc tgacttctcc cctgggtaaa caaacatctc 3360
catcataatc gaaactaaaa cttcaatata agagtggaag agattgaata gaggctgaaa 3420
ttgcattctt caatgaatac ctaagtgtaa aaaagtttaa ttaagtctct ttgaaaattg 3480
aaatgtactc ttaccataaa tttcagattt ccgtgtaagt ccttcttatt aataaagcca 3540
ttcactttct taactgtcat agatctcctt gtctgtatta atatataaat catttgggta 3600
ccaaagtggg attgtgattt tggccatttc tccaaaattg tgaatgaatg aagaaaacaa 3660
tgttagaatt gatcatgttt ttccatctta ttactttggc tcttttttgat ctatagcact 3720
acatttatgt ttatgtggct ctagttcctt cttttgagtgt cttttcttgt gaatcatttt 3780
ttgacctttg cacacataag tcatctgggt gatagagtac ctaatcattt tcttctgcat 3840
aactgcagag tttttttagtt tgtgtttact gtatctccaa tttaatgcat aaaaaagctg 3900
ttgaaaagtt gactgcagaa tgcacataaa ttaacttgtt taaactcatt ttgtccgtca 3960
gctcgatcct atttcctttt agatctgcat aactgcaggg tttttttagtt tgtgtatttt 4020
actgtatctc caatttaatg cattttagct gttgaaaagt tgactgcagc acataaatta 4080
acttgtttaa actcattttg tctgtcagct tgatcctatt tccttttaga atcataatag 4140
ccccaaaact catgactgta atgcatttcc caggaaacag cataacctaa aataacatat 4200
cttattctgt ttttcttcaa ttgtagcttg ccactaggca tggacaccta ttgggggggg 4260
ggggggggat gtctaatttt taataattaa taattttaaa aaatatttat ttttacacat 4320
aaaattgaaa ctaattttta ttttaaatga taataacttt aatcattatc ataaaaacaa 4380
caaacacaaa ttagtttttc acaatttat tcaagtaatc accttaacca ttacagtaat 4440
aataacaagc acaactaatt ttatataatt ttacactaac taactttaat cattattata 4500
ataataacat agataattcg tttttaatag ttttaaatta accaacttaa aaatatatat 4560
ctatgtacat gagaagtgcc aagggaggg ggggtagct gttaaagtaa gtcatagctt 4620
gtttaattat aactataaaa aaatgtttaa atatgttgtg gtgaagtaac tatagcacac 4680
ttgtaaacca tattagcgga gtctgggta catcctctat aaaattacta taatatattc 4740
accaaacaaa ttactaaaat attttgatta aaacatttga aggcctgtaa taagttcgtg 4800
atctgatttg cacttcactt gtatatcaca taacaatcta tgataatatg tccccagcat 4860
ttcttctgct catcggactt ctgtaatttc aggggcagta aagatggaga catatgtgta 4920
gttgaagtaa agaaaatgca gatataccat tatagcaaga gattgcacct gggtacaaat 4980
attgcacnat atctggagtt ctgtcccggg gaaaggtaat ttctatgctc tattggttta 5040
atttggcacc tctgataaat atcaatgtat gcagaatttt agtaattgct gaaacctcct 5100
cctttttgaa tattggacac agttgggatt aagctattca tttgaatatt ggaacatgca 5160
ttgggtacaa aaccttggtg ttagcaatga atttatatta gcaattgatt ttttctcatc 5220
agatcattag ccagagtaaa tgtggatttt tgaaattgaa ccttggtgtt agagaaccaa 5280
tctgacctga aagcttaagt catttataat ggaagttaag tcgttttttt taataaaatta 5340
tagctaacat gcctctgcag attaccttt agtattggat tctgattctg tgatcataca 5400
tagtaatttc tcattttaaa aaaaatacat tcagttaata aatctattct tttggtcttg 5460
cctactcacc caggcttttt ttgttcaggg tttactttac aacctcagta gaatgggggag 5520
cgctggtcac caagctgact gtacctaaag attggaaagg ttctctctct cttacacgca 5580
cacacttgca tgcatcccctt cttcattcta acgccttaca ataatgtcta ttcaatttga 5640
cattttcaat atcctttcaa acctgcagag tggcagatct atttggtgct attgggacta 5700
tttttagcat cagctgtttgc atttacata ttctttgaga actctgattc attctggaac 5760
tttcccatgg gcaaagacca accagcaaga ccaaggttta aacctgtgtt aaaagatccc 5820
cagtcttatg atgaccaaaa tatttggggg ccagtagata tgtgatcaca ttaacattct 5880
tgatttagtc ttcggtgctg ttttggaagc agtatcagta gctgtaactg gtatcaatat 5940
ttatttaagc ccttatagag ttaggcactt gactggtatt acaaacattt acttctattt 6000
ttttggggtg aaaattctga gccaaaggcc atgattggta tgtaatttta atagaaactt 6060
```

-continued

```
taggaataat caaatagctt ccttaaattt acaagttaca cgcaaggctg ctttgtagct   6120
atgtgatggg atccattgaa gaggcacgtc tttggatatc tttccatttt tcttattttg   6180
tttcttgttt taatgataac ctcttacatt ggttttatgc ctttggttag agaaaaataa   6240
a                                                                    6241

Sequence Number (ID): 6
Length: 39
Molecule Type: DNA
Features Location/Qualifiers:
source, 1 . . . 39
mol_type, other DNA
organism, synthetic construct
Residues:
tcaacccggg ggcgcgccat gctctcattt tcgtctctg                             39

Sequence Number (ID): 7
Length: 37
Molecule Type: DNA
Features Location/Qualifiers:
source, 1 . . . 37
mol_type, other DNA
organism, synthetic construct
Residues:
tgccggatcc atttaaatcg aaagagttcg aaaattg                               37

Sequence Number (ID): 8
Length: 41
Molecule Type: DNA
Features Location/Qualifiers:
source, 1 . . . 41
mol_type, other DNA
organism, synthetic construct
Residues:
cgaggctcag caggagaatt catggggaat gatgcagggt c                          41

Sequence Number (ID): 9
Length: 35
Molecule Type: DNA
Features Location/Qualifiers:
source, 1 . . . 35
mol_type, other DNA
organism, synthetic construct
Residues:
gcccttgctc accatcatat ctactggccc ccaaa                                 35

Sequence Number (ID): 10
Length: 22
Molecule Type: DNA
Features Location/Qualifiers:
source, 1 . . . 22
mol_type, other DNA
organism, synthetic construct
Residues:
tggaaaaga agcgaactgg gt                                                 22

Sequence Number (ID): 11
Length: 22
Molecule Type: DNA
Features Location/Qualifiers:
source, 1 . . . 22
mol_type, other DNA
organism, synthetic construct
Residues:
gcttccaaca cataagtggt ca                                                22

Sequence Number (ID): 12
Length: 20
Molecule Type: DNA
Features Location/Qualifiers:
source, 1 . . . 20
mol_type, other DNA
organism, synthetic construct
Residues:
tgcaaaggag gctgctaact                                                   20

Sequence Number (ID): 13
Length: 20
Molecule Type: DNA
Features Location/Qualifiers:
```

-continued

```
source, 1 . . . 20
mol_type, other DNA
organism, synthetic construct
Residues:
cagcatcacc gttcttcaaa                                        20

Sequence Number (ID): 14
Length: 51
Molecule Type: DNA
Features Location/Qualifiers:
source, 1 . . . 51
mol_type, other DNA
organism, synthetic construct
Residues:
cgaggctcag caggaggcgc gccggacatg tgcaccacga ggaatattag g     51

Sequence Number (ID): 15
Length: 28
Molecule Type: DNA
Features Location/Qualifiers:
source, 1 . . . 28
mol_type, other DNA
organism, synthetic construct
Residues:
tcgcgctaat gccgcggaat cttaagcg                               28

Sequence Number (ID): 16
Length: 41
Molecule Type: DNA
Features Location/Qualifiers:
source, 1 . . . 41
mol_type, other DNA
organism, synthetic construct
Residues:
cgaggctcag caggagaatt ccggaatctt aagcgaatat c                41

Sequence Number (ID): 17
Length: 43
Molecule Type: DNA
Features Location/Qualifiers:
source, 1 . . . 43
mol_type, other DNA
organism, synthetic construct
Residues:
tgcatcattc cccatcgaaa gtgttcgaaa attggatacc cag              43

Sequence Number (ID): 18
Length: 28
Molecule Type: DNA
Features Location/Qualifiers:
source, 1 . . . 28
mol_type, other DNA
organism, synthetic construct
Residues:
cgcttaagat tccgcggcat tagcgcga                               28

Sequence Number (ID): 19
Length: 43
Molecule Type: DNA
Features Location/Qualifiers:
source, 1 . . . 43
mol_type, other DNA
organism, synthetic construct
Residues:
ttacaattac catggggcgc gccatgggga atgatgcagg gtc              43

Sequence Number (ID): 20
Length: 35
Molecule Type: DNA
Features Location/Qualifiers:
source, 1 . . . 35
mol_type, other DNA
organism, synthetic construct
Residues:
ttacaattac catggcggaa tcttaagcga atatc                       35

Sequence Number (ID): 21
Length: 50
Molecule Type: DNA
```

-continued

```
Features Location/Qualifiers:
source, 1 . . . 50
mol_type, other DNA
organism, synthetic construct
Residues:
ttacaattac catggcggaa tcttaagcga atatctccat agttgctaat            50

Sequence Number (ID): 22
Length: 45
Molecule Type: DNA
Features Location/Qualifiers:
source, 1 . . . 45
mol_type, other DNA
organism, synthetic construct
Residues:
atatctccat agttgctaat atgttttgtt tcttccagcg ttgtt                 45

Sequence Number (ID): 23
Length: 25
Molecule Type: DNA
Features Location/Qualifiers:
source, 1 . . . 25
mol_type, other DNA
organism, synthetic construct
Residues:
cttcaatttt ttaaaccctc aaaat                                       25

Sequence Number (ID): 24
Length: 58
Molecule Type: DNA
Features Location/Qualifiers:
source, 1 . . . 58
mol_type, other DNA
organism, synthetic construct
Residues:
ttacaattac catggcggaa tcttaagcga atatctccat agttgctaat aaattttg   58

Sequence Number (ID): 25
Length: 33
Molecule Type: DNA
Features Location/Qualifiers:
source, 1 . . . 33
mol_type, other DNA
organism, synthetic construct
Residues:
tgcatcattc cccatcgaaa gtgttcgaaa att                              33

Sequence Number (ID): 26
Length: 25
Molecule Type: DNA
Features Location/Qualifiers:
source, 1 . . . 25
mol_type, other DNA
organism, synthetic construct
Residues:
attttgaggg tttaaaaaat tgaag                                       25

Sequence Number (ID): 27
Length: 360
Molecule Type: AA
Features Location/Qualifiers:
source, 1 . . . 360
mol_type, AA
organism, Glycine max
Residues:
MGNDAGSPQG PVTCGSWIRR PENLNLVVLG RSRRGNSCPS LLEIFSFDPK TTSLSTCPLT   60
TYVLEAEEGD PVAIAVHPSG DDFVCALSNG SCKLFELYGR ETNMKLLAKE LAPLQGIGPQ  120
KCIAFSVDGS KFAAGGLDGH LRIMEWPSMR VILDEPRAHK SVRDMDFSLD SEFLASTSTD  180
GSARIWKIED GVPLTTLSRN SDEKIELCRF SKDGTKPFLF CSVQKGDTSV TAVYEISTWN  240
KIGHKRLIRK SASVMSISHD GKYLSLGSKD GDICVVEVKK MQIYHYSKRL HLGTNIAYLE  300
FCPGERVLLT TSVEWGALVT KLTVPKDWKE WQIYLVLLGL FLASAVAFYI FFENSDSFWN  360
END
```

What is claimed is:

1. A method for analysing phosphorus acquisition efficiency in a soybean plant, the method comprising:

(a) transforming a soybean plant of variety YC04-5 with a recombinant RNAi interference construct comprising a cDNA sequence of a SEC-12 like protein gene CPU1 as shown in SEQ ID No: 2, wherein the RNAi construct is operably linked to a promoter to produce a transgenic soy bean plant expressing the RNAi Construct;

(b) inhibiting expression of the CPU1 gene in the transgenic soybean plant by expression of the RNAi construct; and (c) measuring the phosphorus acquisition efficiency of the transgenic soybean plant to analyze the function of the CPU1 gene in phosphorus acquisition.

2. The method according to claim 1, wherein the RNAi construct comprises a forward fragment and a reverse fragment, cloned in forward and reverse orientations.

3. The method according to claim 1, wherein the forward fragment and the reverse fragment are cloned using Swa I+Asc I and Sma I+BamH1 enzyme digestions of an amplified 147 bp fragment of a cDNA sample as sequenced in the cDNA sequence as shown in SED ID No: 2.

4. The method according to claim 1, wherein the *Agrobacterium tumefaciens*-mediated transformation uses an EHA 105 strain.

5. The method according to claim 1, wherein the promoter is a constitutive promoter.

6. The method according to claim 1, wherein the transgenic soybean plant comprises recombinant vectors and resulting expression products of a foreign gene.

* * * * *

SEQUENCE LISTING

Sequence total quantity: 27
SEQ ID NO: 1              moltype = DNA   length = 6238
FEATURE                   Location/Qualifiers
source                    1..6238
                          mol_type = genomic DNA
                          organism = Glycine max
SEQUENCE: 1
cggaatctta agcgaatatc tccatagttg ctaatatgtt ttgtttcttc cagcattgtt   60
gcatttactg gacccatctc tcccttcttt ctattaaaca aatcgcttca attttttcaa  120
ccctcaaaat taatcaactt tcattttttt tataaatcca acccctaaa catattttca   180
cattgcgttc aagcaacagt tgcatcatcc taataaaacc ctgtgatcat atacattcat  240
actcagcaac cttaaaacac aatatcacgt aaaaaaggtg agacatgtct ttttcgaacg  300
cgtgacatta attaataagg ctgtgccttg tttcattggt taattaatta atgattaaat  360
aaagcaaggc aaagctcttt ctatcttcct ttgacttttt ttttcagagg ctctatttt   420
cttctctgac atttctattt aaatttgccg aagaatccaa ttcaccgatc tccgaagagc  480
tccatttgga aaaagaagcg aactgggtat ccaattttcg aacacttcg atggggaatg   540
atgcagggtc acctcagggt ccggttacgt gtgggtcgtg gattcggagg cctgagaatt  600
tgaacttggt ggtgttagga aggtccagac gtggcaattc ttgtccttct ctcttggaga  660
ttttctcctt cgatcccaag accacttctc tgtctacctg tcctctggta ttcctctaaa  720
actctgaata tacatacacg tatcatgtgt gtgtgtgttg tgtttaagta tgcatgtgcg  780
tgtgtaattt attttatatt atgtatagag tgactcattt gtaacattaa tttgttttgt  840
gcagaccctt tttattgtat gttgaaaaac tgttgttttc tttgtgttat gtttgtgtat  900
gtctgagcat gtagattctg tggagtgagt catttgaaac gcgagccttt ttgtgcatat  960
acttttgat tattggccga gaaactgttt actttttcct ctctgaagca gatggtgggt  1020
ggaagtagat attatgcaca aattctgttg ttgaaaagta tttttagtgt tgaaattctg  1080
ggttgctgaa tggaagcaaa gtttgaatgg gctatggctt tggtttttaat gatgtttttg  1140
ttttgatatt tcagaccact tatgtgttgg aagcagagga aggtgatcct gttgctattg  1200
cagtccaccc aagtggggat gattttgtgt gcgctctcag caatggtagc tgcaagtaag  1260
tttcttttgt aagggcttcg agattgaagc gttctttat atgtattcat cttttgaaat  1320
acttccgtga tgtgtctcaa cttgcatttc taaaattagc agttcacttg cgataatctc  1380
agaaacagac tccaacattt tatctttctt taaccgttca aagtacaaga taaaactgta  1440
ggctcagttc taccaaattt ctctctgaca gtttctcgtt cctttttttt ttttccctgg  1500
gaactaggga atgtttgaca taatagttat tgttgtttct taggtataga tagatgaatt  1560
ttgccttgag ttatttttcgt tggatgatt gtgccatcct tggatagtta agatcctaca  1620
cnatcagtta ggtatatggc aatagcttta gaggtagagt tagactcatt tcattctcaa  1680
ttctaatatg atatcaaagc gtattcaggc ctgatgtttg accacctgca catgtctggt  1740
gcagcctaca aacttcatgc tctagcctct agatgtctag tcctggacat gatatcctcc  1800
catgattctt atttctaatt gatactgaac tgaacatata atatagattg aagtatttct  1860
ccatggcttg tagattgttt gagctgtatg gtcgtgaaac aaacatgaag ttgttggcta  1920
aggaactggc tcctctacag ggtattggtc ctcagaaatg cattgctttt agtgttgatg  1980
ggtctaaatt tgctgctggt gggttggtaa gcatcacttt atatccaacc aattgctttt  2040
attttctatt cagcactttg agttttcct tttcaagttt gatcttgtat gtttgactc   2100
tgtctttaac aagtgtagga tggacatctc agaattatgg agtggcctag tatgcgcgtg  2160
attttggatg aaccaagagc acacaaatca gttcgggata tggattttag gtaggtatag  2220
taaacaaatc tatttggatc cttctaaagg aggcatcaat ccctacagct agtaaaattg  2280
taataaaatag ttgataaagt tggttactat agtaatgtta tttcgagttc ttacaaccag  2340
ataagataat ttttgctttg catgttcatg cctgcaataa cttgactgtg tagatatgat  2400
ctttagaaa ataaaagtat gttacattgt aaatattta atcctgaaac tttaatgata  2460
ttgtacttac tatattgtcc ttcatttttt cccttacttt agtctagact cagaatttct  2520
agcttcaact tctactgatg gttcagcaag aatctggaag attgaagatg gtgttccttt  2580
gactactttg tctcgcaact cggtatggtg tatttgattt aagaacctgg ggcaagatct  2640
gtatgcagta cttgtattgc ttgatccaaa tatttccttt tgtctcttta ggatgaaaag  2700
attgaattat gtcgattttc catggatgga accaaaccat ttttattttg ctctgttcaa  2760
aaaggtataa gagtatcttg tttctagtat attctatagt attaatttgt atattcttca  2820
aatctctttg accagcaaag catggccttt ataatagata cttatatctt ttagcaggtg  2880
atacttctgt cactgcggtt tatgagatta gcacatggaa taaaattggg cacaagaggc  2940
tgattagaaa gtctgcttca gtaatgtcca ttagccatga tgggaaatac cttttctctgt  3000
aagaacctgc agttatcttc tgactttttg gcttatgtgt ggtcattggt caacattctt  3060
cctttatctt tcgttagttt tgatttccaa attttatcca gatagttttg tgactattgt  3120
aagtcttgca tcttaagcaa gtgaataatt tagaattttt atttcttttg ttttgaccaa  3180
tagaattttt attcaattgc cttctgttat cctcagcagt ctgcatgctt gaaggagtgc  3240
ttgaatcccc ctcccccatg cattatctga tgtaggaatg taaatatccc aatctcaaaaa  3300
tgttgaccag gaggtctttc gtttacctga cttctcccct gggtaaacaa acatctccat  3360
cataatcgaa actaaaactt caatataaga gtggaagaga ttgaatagag ctgaaattg   3420
cattcttcaa tgaatacctta agtgtaaaaa agtttaatta agtctctttg aaaattgaaa  3480
tgtactctta ccataaattt cagatttccg tgtaagtcct tcttattaat aaagccattc  3540
actttcttaa ctgtcataga tctccttgtc tgtattaata tataaatcat ttgggtacca  3600
aagtgggatt gtgatttttgg ccatttctcc aaaattgtga atgaatgaag aaaacaatgt  3660
tagaattgat catgttttc catcttatta ctttggctct ttttgatcta tagcactaca  3720
tttatgttta tgtggctcta gttccttctt tgagtgtctt ttcttgtgaa tcattttttg  3780
acctttgcac acataagtca tctgggtgat agactaccta atcattttct tctgcataac  3840
tgcagagttt tttagtttgt gtttactgta tctccaattt aatgcataaa aaagctgttg  3900
aaaagttgac tgcagaatgc acataaaatta acttgtttaa actcattttg tccgtcagct  3960
cgacnatcct atttccttt agatctgcat aactgcaggg ttttttagtt tgtgtatttt   4020
actgtatctc caatttaatg cattttagct gttgaaaagt tgactgcagc acataaaatta  4080
acttgtttaa actcattttg tctgtcagct tgatcctatt tccttttaga atcataatag  4140
ccccaaaact catgactgta atgcatttcc caggaaacag cataacctaa aataacatat  4200
cttattctgt ttttcttcaa ttgtagcttg ccactaggca tggacaccta ttggggggggg  4260

-continued

```
gggggggggat gtctaatttt taataattaa taattttaaa aaatatttat ttttacacat   4320
aaaattgaaa ctaatttta ttttaaatga taataacttt aatcattatc ataaaaacaa    4380
caaacacaaa ttagtttttc acaattttat tcaagtaatc accttaacca ttacagtaat   4440
aataacaagc acaactaatt ttatataatt ttacactaac taactttaat cattattata   4500
ataataacat agataaattcg tttttaatag ttttaaatta accaacttaa aaatatatat   4560
ctatgtacat gagaagtgcc aagggagggg gggggtagct gttaaagtaa gtcatagctt   4620
gtttaattat aactataaaa aaatgtttaa atatgttgtg gtgaagtaac tatagcacac   4680
ttgtaaacca tattagcgga gtctgggta catcctctat aaaattacta taatatattc     4740
accaaacaaa ttactaaaat attttgatta aaacatttga aggcctgtaa taagttcgtg   4800
atctgatttg cacttcactt gtatatcaca taacaatcta tgataatatg tccccagcat   4860
ttcttctgct catcggactt ctgtaatttc aggggcagta aagatggaga catatgtgta   4920
gttgaagtaa agaaaatgca gatataccat tatagcaaga gattgcacct gggtacaaat   4980
attgcatatc tggagttctg tcccgggaa aggtaatttc tatgctctat tggtttaatt    5040
tggcacctct gataaaatatc aatgtatgca gaattttagt aattgctgaa acctcctcct   5100
ttttgaatat tggacacagt tgggattaag ctattcattt gaatattgga acatgcattg    5160
ggtacaaaac cttggtgtta gcaatgaatt tatattagca attgatttt tctcatcaga     5220
tcattagcca gagtaaatgt ggattttga aattgaacct tggtgttaga gaaccaatct     5280
gacctgaaag cttaagtcat ttataatgga agttaagtcg tttttttaa taaattatag     5340
ctaacatgcc tctgcagatt accttttagt attggattct gattctgtga tcatacatag    5400
taatttctca ttttaaaaaa aatacattca gttaataaat ctattctttt ggtcttgcct    5460
actcacccag gctttttttg ttcagggttt tacttacaac ctcagtagaa tggggagcgc     5520
tggtcaccaa gctgactgta cctaaagatt ggaaaggttc tctctctctt acacgcacac    5580
acttgcatgc atcccttctt cattctaacg ccttacaata atgtctattc aatttgacat     5640
tttcaatatc ctttcaaacc tgcagagtgg cagatctatt tggtgctatt gggactattt    5700
ttagcatcag ctgttgcatt ttacatattc tttgagaact ctgattcatt ctggaacttt    5760
cccatgggca aagaccaacc agcaagacca aggtttaaa ctgtgttaaa agatccccag      5820
tcttatgatg accaaaatat ttgggggcca gtagatatg gatcacatta acattccttga    5880
tttagtcttc ggtgctgttt tggaagcagt atcagtagct gtaactggta tcaatattta    5940
tttaagccct tatagagtta ggcacttgac tggtattaca aacatttact tctatttttt    6000
tggggtgaaa attctgagcc aaaggccatg attggtatgt aattttaata gaaactttag    6060
gaataatcaa atagcttcct taaatttaca agttacacgc aaggctgctt tgtagctatg    6120
tgatgggatc cattgaagag gcacgtcttt ggatatcttt ccatttttct tattttgttt    6180
cttgtttttaa tgataacctc ttacattggt tttatgcctt tggttagaga aaaataaa     6238
```

```
SEQ ID NO: 2         moltype = DNA  length = 1915
FEATURE              Location/Qualifiers
source               1..1915
                     mol_type = genomic DNA
                     organism = Glycine max
SEQUENCE: 2
cggaatctta agcgaatatc tccatagttg ctaatatgtt ttgtttcttc cagcattgtt      60
gcatttactg gacccatctc tcccttcttt ctattaaaca aatcgcttca attttttcaa    120
ccctcaaaat taatcaactt tcattttttt tataaatcca acccctaaa catattttca      180
cattgcgttc aagcaacagt tgcatcatcc taataaaacc ctgtgatcat atacattcat     240
actcagcaac cttaaaacac aatatcacgt aaaaaagaat ccaattcacc gatctccgaa     300
gagctccatt tggaaaaaga agcgaactgg gtatccaatt ttcgaacact ttcgatgggg      360
aatgatgcag ggtcacctca gggtccggtt acgtgtgggt cgtggattcg gaggcctgag    420
aatttgaact tggtggtgtt aggaaggtcc agacgtggca attcttgtcc ttctctcttg    480
gagattttct ccttcgatcc caagaccact tctctgtcta cctgtcctct gaccacttat    540
gtgttggaag cagaggaagg tgatcctgtt gctattgcag tccacccaag tggggatgat     600
tttgtgtgcg ctctcagcaa tggtagctgc aaattgtttg agctgtatgg tcgtgaaaca    660
aacatgaagt tgttggctaa ggaactggct cctctacagg gtattggtcc tcagaaatgc     720
attgctttta gtgttgatgg gtctaaattt gctgctggtg ggttggatgg acatctcaga    780
attatggagt ggcctagtat gcgcgtgatt ttggatgaac caagagcaca caaatcagtt    840
cgggatatgg attttagtct agactcagaa tttctagctt caacttctac tgatggttca    900
gcaagaatct ggaagattga agatggtgtt cctttgacta ctttgtctcg caactcggat    960
gaaaagattg aattatgtcg attttccatg gatggaacca aaccattttt attttgctct    1020
gttcaaaaag gtgatacttc tgtcactgcg gtttatgaga ttagcacatg gaataaaatt   1080
gggcacaaga ggctgattag aaagtctgct tcagtaatgt ccattagcca tgatgggaaa   1140
tacctttctc tgggcagtaa agatggagac atatgtgtag ttgaagtaaa gaaaatgcag  1200
atataccatt atagcaagag attgcacctg gtacaaata ttgcatatct ggagttctgt    1260
cccgggaaa gggttttact tacaacctca gtagaatggg gagcgctggt caccaagctg    1320
actgtaccta aagattggaa agagtggcag atctatttgg tgctattggg actatttta    1380
gcatcagctg ttgcatttta catattcttt gagaactctg attcattctg gaacttttcc   1440
atgggcaaag accaaccagc aagaccaagg tttaaacctg tgttaaaaga tccccagtct   1500
tatgatgacc aaaatatttg ggggccagta gatatgtgat cacattaaca ttcttgattt   1560
agtcttcggt gctgttttgg aagcagtatc agtagctgta actggtatca atatttattt   1620
aagcccttat agagttaggc acttgactgg tattacaaac atttacttct atttttttgg   1680
ggtgaaaatt ctgagccaaa ggccatgatt ggtatgtaat tttaatagaa actttaggaa   1740
taatcaaata gcttccttaa atttacaagt tacacgcaag gctgctttgt agctatgtga   1800
tgggatccat tgaagaggca cgtcttggga tatcttccca ttttttcttat tttgtttctt   1860
gtttttaatga taacctctta cattggtttt atgcctttgg ttagagaaaa ataaa        1915
```

```
SEQ ID NO: 3         moltype = DNA  length = 120
FEATURE              Location/Qualifiers
source               1..120
                     mol_type = genomic DNA
                     organism = Glycine max
SEQUENCE: 3
```

-continued

```
atgttttgtt tcttccagca ttgttgcatt tactggaccc atctctccct tctttctatt   60
aaacaaatcg cttcaatttt ttcaaccctc aaaattaatc aactttcatt tttttatataa  120

SEQ ID NO: 4        moltype = DNA  length = 1185
FEATURE             Location/Qualifiers
source              1..1185
                    mol_type = genomic DNA
                    organism = Glycine max
SEQUENCE: 4
atggggaatg atgcagggtc acctcagggt ccggttacgt gtgggtcgtg gattcggagg   60
cctgagaatt tgaacttggt ggtgttagga aggtccagac gtggcaattc ttgtccttct  120
ctcttggaga ttttctcctt cgatcccaag accacttctc tgtctacctg tcctctgacc  180
acttatgtgt tggaagcaga ggaaggtgat cctgttgcta ttgcagtcca cccaagtggg  240
gatgattttg tgtgcgctct cagcaatggt agctgcaaat tgtttgagct gtatggtcgt  300
gaaacaaaca tgaagttgtt ggctaaggaa ctggctcctc tacagggtat tggtcctcag  360
aaatgcattg cttttagtgt tgatgggtct aaatttgctg ctggtgggtt ggatggacat  420
ctcagaatta tggagtggcc tagtatgcgc gtgattttgg atgaaccaag agcacacaaa  480
tcagttcggg atatggattt tagtctagac tcagaatttc tagcttcaac ttctactgat  540
ggttcagcaa gaatctggaa gattgaagat ggtgttcctt tgactacttt gtctcgcaac  600
tcggatgaaa agattgaatt atgtcgattt tccatggatg gaaccaaacc atttttattt  660
tgctctgttc aaaaaggtga tacttctgtc actgcggttt atgagattag cacatggaat  720
aaaattgggc acaagaggct gattagaaag tctgcttcag taatgtccat tagccatgat  780
gggaaatacc tttctctggg cagtaaagat ggagacatat gtgtagttga agtaaagaaa  840
atgcagatat accattatag caagagattg cacctgggta caaatattgc atatctggag  900
ttctgtcccg gggaaagggt tttacttaca acctcagtaa aatggggagc gctggtcacc  960
aagctgactg tacctaaaga ttggaaagag tggcagatct atttggtgct attgggacta 1020
tttttagcat cagctgttgc attttacata ttctttgaga actctgattc attctggaac 1080
tttcccatgg gcaaagacca accagcaaga ccaaggttta aacctgtgtt aaaagatccc 1140
cagtcttatg atgaccaaaa tatttggggg ccagtagata tgtga             1185

SEQ ID NO: 5        moltype = DNA  length = 6241
FEATURE             Location/Qualifiers
source              1..6241
                    mol_type = genomic DNA
                    organism = Glycine max
SEQUENCE: 5
cggaatctta agcgaatatc tccatagttg ctaaatatgtt ttgtttcttc cagcgttgtt   60
gcatttactg gacccatctc tcccttcttt ctattaaaca aatcgcttaa attttttaaa  120
ccctcaaaat taatcaactt tcattttttt tataaatcca acccctaaa catatttca  180
cattgcgttc aagcaacagt tgcatcatcc taataaaacc ctgtgatcat atacattcat  240
actcagcaac cttaaaacac aatatcacgt aaaaaaggtg agacatgtct ttttcgaacg  300
cnacgtgaca ttaattaata aggctgtgcc ttgtttcatt ggttaattaa ttaatgatta  360
aataaagcaa ggcaaagctc tttctatctt cctttgactt tttttttcag aggctctatt  420
tttcttctct gacatttcta tttaaatttg ccgaagaatc caattcaccg atctccgaag  480
agctccattt ggaaaaagaa gcgaactggg tatccaattt tcgaacactt tcgatgggga  540
atgatgcagg gtcacctcag ggtccggtta cgtgtgggtc gtggattcgg aggcctgaga  600
atttgaactt ggtggtgtta ggaaggtcca gacgtggcaa ttcttgtcct tctctcttgg  660
agattttctc cttcgatccc aagaccactc tctgtctac ctgtcctctg gtattcctct  720
aaaactctga atatacatac acgtatcatg tgtgtgtgtg ttgtgtttaa gtatgcatgt  780
gcgtgtgtaa tttattttat attatgtata gagtgactca tttgtaacat taatttgttt  840
tgtgcagacc cttttttattg tatgttgaaa aactgttgtt ttctttgtgt tatgtttgtg  900
tatgtctgag catgtagatt ctgtggagtg agtcatttga aacacgagcc ttttttgtgca  960
tatactttt gattattggc cgagaaactg tttactttt cctctctgaa gcagatggtg 1020
ggtggaagta gatattatgc acaaattctg ttgttgaaaa gtattttag tgttgaaatt 1080
ctgggtgct gaatggaagc aaagtttgaa tgggctatgg cttttggtttt aatgatgttt 1140
ttgtttttgat atttcagacc acttatgtgt tggaagcaga ggaaggtgat cctgttgcta 1200
ttgcagtcca cccaagtggg gatgattttg tgtgcgctct cagcaatggt agctgcaagt 1260
aagtttcttt tgtaagggct tcgagattga agcgttcttt tatatgtatt catcttttga 1320
aatacttccg tgatgtgtct caacttgcat ttctaaaatt agcagttcac ttgcgataat 1380
ctcagaaaca gactccaaca ttttatcttt ctttaaccgt tcaaagtaca agataaaact 1440
gtaggctcag ttctaccaaa tttctctctg acagttctc gttcctttt tttttttccc 1500
tgggaactag ggaatgtttg acataatagt tattgttgtt tcttaggtat agatagatga 1560
attttgcctt gagttatttt cgttggatga tttgtgccat ccttggatag ttaagatcct 1620
acatcagtta ggtatatggc aatagcttta gaggtagagt tagactcatt tcattctcaa 1680
ttctaatatg atatcaaagc gtattcaggc ctgatgtttg accacctgca catgtctggt 1740
gcagcctaca aacttcatgc tctagcctct agatgtctag tcctggacat gatatcctcc 1800
catgattctt atttctaatt gatactgaac tgaacatata atatagattg aagtatttct 1860
ccatggcttg tagattgttt gagctgtatg gtcgtgaaac aaacatgaag ttgttggcta 1920
aggaactggc tcctctacag ggtattggtc ctcagaaatg cattgctttt agtgttgatg 1980
ggtctaaatt tgctgctggt gggttggtaa gcatcacttt tatatccaacc aattgctttt 2040
attttctatt cagcactttg agtttttcct tttcaagttt gatcttgtat gtttgacttc 2100
tgtctttaac aagtgtagga tggacatctc agaattatgg agtggcctag tatgcgcgtg 2160
attttggatg aaccaagagc acacaaatca gttcgggata tggattttag gtaggtatag 2220
taaacaaatc tatttggatc cttctaaagg aggcatcaat ccctacagct agtaaaattg 2280
taataaaatag ttgataaagt tggttactat agtaatgata tttcgagttc ttacaaccag 2340
ataagataat ttttgtcttg catgttcatg cctgcaataa cttgactgtg tagatatgat 2400
cttttagaaa ataaaagtat gttacattgt aaatatttta atcctgaaac tttaatgata 2460
ttgtacttac tatattgtcc ttcattttt cccttacttt agtctagact cagaatttct 2520
agcttcaact tctactgatg gttcagcaag aatctggaag attgaagatg gtgttccttt 2580
```

-continued

```
gactactttg tctcgcaact cggtatggtg tatttgattt aagaacctgg ggcaagatct    2640
gtacnatgca gtacttgtat tgcttgatcc aaatatttcc ttttgtctct ttaggatgaa    2700
aagattgaat tatgtcgatt ttccatggat ggaaccaaac catttttatt ttgctctgtt    2760
caaaaaggta taagagtatc ttgtttctag tatattctat agtattaatt tgtatattct    2820
tcaaatctct ttgaccagca aagcatggcc tttataatag atacttatat cttttagcag    2880
gtgatacttc tgtcactgcg gtttatgaga ttagcacatg gaataaaatt gggcacaaga    2940
ggctgattag aaagtctgct tcagtaatgt ccattagcca tgatgggaaa tacctttctc    3000
tgtaagaacc tgcagttatc ttctgacttt ttggcttatg tgtggtcatt ggtcaacatt    3060
cttcctttat ctttcgttag ttttgatttc caaattttat ccagatagtt ttgtgactat    3120
tgtaagtctt gcatcttaag caagtgaata atttagaatt tttatttctt ttgtttttgac    3180
caatagaatt tttattcaat tgccttctgt tatcctcagc agtctgcatg cttgaaggag    3240
tgcttgaatc cccctccccc atgcattatc tgatgtagga atgtaaatat cccaatctaa    3300
aaatgttgac caggaggtct ttcgtttacc tgacttctcc cctgggtaaa caaacatctc    3360
catcataatc gaaactaaaa cttcaatata agagtggaag agattgaata gagagctgaaa   3420
ttgcattctt caatgaatac ctaagtgtaa aaaagtttaa ttaagtctct ttgaaaattg    3480
aaatgtactc ttaccataaa tttcagattt ccgtgtaagt ccttcttatt aataaagcca    3540
ttcactttct taactgtcat agatctcctt gtctgtatta atatataaat catttgggta    3600
ccaaagtggg attgtgattt tggccatttc tccaaaattg tgaatgaatg aagaaaacaa    3660
tgttagaatt gatcatgttt ttccatctta ttactttggc tctttttgat ctatagcact    3720
acatttatgt ttatgtggct ctagttcctt ctttgagtgt cttttcttgt gaatcatttt    3780
ttgacctttg cacacataag tcatctgggt gatagactac ctaatcattt tcttctgcat    3840
aactgcagag ttttttagtt tgtgtttact gtatctccaa tttaatgcat aaaaaagctg    3900
ttgaaaagtt gactgcagaa tgcacataaa ttaacttgtt taaactcatt ttgtccgtca    3960
gctcgatcct atttccttt agatctgcat aactgcaggg tttttttagtt tgtgtatttt   4020
actgtatctc caatttaatg cattttagct gttgaaaagt tgactgcagc acataaatta    4080
acttgtttaa actcattttg tctgtcagct tgatcctatt tccttttaga atcataatag    4140
ccccaaaact catgactgta atgcatttcc caggaaacag cataacctaa aataacatat    4200
cttattctgt ttttcttcaa ttgtagcttg ccactaggca tggacaccta ttgggggggg    4260
ggggggggat gtctaatttt taataattaa taattttaaa aaatatttat ttttacacat    4320
aaaattgaaa ctaatttta ttttaaatga taataacttt aatcattatc ataaaaacaa    4380
caaacacaaa ttagtttttc acaattttat tcaagtaatc accttaacca ttacagtaat    4440
aataacaagc acaactaatt ttatataatt ttacactaac taactttaat cattattata    4500
ataataacat agataattcg tttttaatag ttttaaatta accaacttaa aaatatatat    4560
ctatgtacat gagaagtgcc aagggagggg gggggtagct gttaaagtaa gtcatagctt    4620
gtttaattat aactataaaa aaatgtttaa atatgttgtg gtgaagtaac tatagcacac    4680
ttgtaaacca tattagcgga gtctgggta catcctctat aaaattacta taatatattc    4740
accaaacaaa ttactaaaat attttgatta aaacatttga aggcctgtaa taagttcgtg    4800
atctgatttg cacttcactt gtatatcaca taacaatcta tgataatatg tccccagcat    4860
ttcttctgct catcggactt ctgtaatttc aggggcagta aagatggaga catatgtgta    4920
gttgaagtaa agaaaatgca gatataccat tatagcaaga gattgcacct gggtacaaat    4980
attgcacnat atctggagtt ctgtcccggg gaaaggtaat ttctatgctc tattggttta    5040
atttggcacc tctgataaat atcaatgtat gcagaatttt agtaattgct gaaacctcct    5100
ccttttgaa tattggacac agttgggatt aagctattca tttgaatatt ggaacatgca    5160
ttgggtacaa aaccttggtg ttagcaatga atttatatta gcaattgatt ttttctcatc    5220
agatcattag ccagagtaaa tgtggatttt tgaaattgaa ccttggtgtt agagaaccaa    5280
tctgacctga aagcttaagt catttataat ggaagttaag tcgttttttt taataaatta    5340
tagctaacat gcctctgcag attacctttt agtattggat tctgattctg tgatcataca    5400
tagtaatttc tcattttaaa aaaaatacat tcagttaata aatctattct tttggtcttg    5460
cctactcacc caggcttttt ttgttcaggg ttttacttac aacctcagta gaatggggag    5520
cgctggtcac caagctgact gtacctaaag attggaaagg ttctctctct cttacacgca    5580
cacacttgca tgcatcccttt cttcattcta acgccttaca ataatgtcta ttcaatttga    5640
cattttcaat atcctttcaa acctgcagag tggcagatct atttggtgct attgggacta    5700
tttttagcat cagctgttgc attttacata ttctttgaga actctgattc attctggaac    5760
tttcccatgg gcaaagacca accagcaaga ccaaggttta aacctgtgtt aaaagatccc    5820
cagtcttatg atgaccaaaa tatttggggg ccagtagata tgtgatcaca ttaacattct    5880
tgatttagtc ttcggtgctg tttttggaagc agtatcagta gctgtaactg gtatcaatat    5940
ttatttaagc ccttatagag ttaggcactt gactggtatt acaaacattt acttctattt    6000
ttttgggggtg aaaattctga gccaaaggcc atgattggta tgtaattta atagaaactt    6060
taggaataat caaatagctt ccttaaattt acaagttaca cgcaaggctg ctttgtagct    6120
atgtgatggg atccattgaa gaggcacgtc tttggatatc tttccatttt tcttattttg    6180
tttcttgttt taatgataac ctcttacatt ggttttatgc ctttggttag agaaaaataa    6240
a                                                                    6241
```

SEQ ID NO: 6          moltype = DNA   length = 39
FEATURE               Location/Qualifiers
source                1..39
                      mol_type = other DNA
                      organism = synthetic construct
SEQUENCE: 6
tcaacccggg ggcgcgccat gctctcattt tcgtctctg                          39

SEQ ID NO: 7          moltype = DNA   length = 37
FEATURE               Location/Qualifiers
source                1..37
                      mol_type = other DNA
                      organism = synthetic construct
SEQUENCE: 7
tgccggatcc atttaaatcg aaagagttcg aaaattg                            37

-continued

```
SEQ ID NO: 8              moltype = DNA   length = 41
FEATURE                   Location/Qualifiers
source                    1..41
                          mol_type = other DNA
                          organism = synthetic construct
SEQUENCE: 8
cgaggctcag caggagaatt catggggaat gatgcagggt c              41

SEQ ID NO: 9              moltype = DNA   length = 35
FEATURE                   Location/Qualifiers
source                    1..35
                          mol_type = other DNA
                          organism = synthetic construct
SEQUENCE: 9
gcccttgctc accatcatat ctactggccc ccaaa                     35

SEQ ID NO: 10             moltype = DNA   length = 22
FEATURE                   Location/Qualifiers
source                    1..22
                          mol_type = other DNA
                          organism = synthetic construct
SEQUENCE: 10
tggaaaaaga agcgaactgg gt                                    22

SEQ ID NO: 11             moltype = DNA   length = 22
FEATURE                   Location/Qualifiers
source                    1..22
                          mol_type = other DNA
                          organism = synthetic construct
SEQUENCE: 11
gcttccaaca cataagtggt ca                                    22

SEQ ID NO: 12             moltype = DNA   length = 20
FEATURE                   Location/Qualifiers
source                    1..20
                          mol_type = other DNA
                          organism = synthetic construct
SEQUENCE: 12
tgcaaaggag gctgctaact                                       20

SEQ ID NO: 13             moltype = DNA   length = 20
FEATURE                   Location/Qualifiers
source                    1..20
                          mol_type = other DNA
                          organism = synthetic construct
SEQUENCE: 13
cagcatcacc gttcttcaaa                                       20

SEQ ID NO: 14             moltype = DNA   length = 51
FEATURE                   Location/Qualifiers
source                    1..51
                          mol_type = other DNA
                          organism = synthetic construct
SEQUENCE: 14
cgaggctcag caggaggcgc gccggacatg tgcaccacga ggaatattag g    51

SEQ ID NO: 15             moltype = DNA   length = 28
FEATURE                   Location/Qualifiers
source                    1..28
                          mol_type = other DNA
                          organism = synthetic construct
SEQUENCE: 15
tcgcgctaat gccgcggaat cttaagcg                              28

SEQ ID NO: 16             moltype = DNA   length = 41
FEATURE                   Location/Qualifiers
source                    1..41
                          mol_type = other DNA
                          organism = synthetic construct
SEQUENCE: 16
cgaggctcag caggagaatt ccggaatctt aagcgaatat c              41

SEQ ID NO: 17             moltype = DNA   length = 43
FEATURE                   Location/Qualifiers
source                    1..43
                          mol_type = other DNA
                          organism = synthetic construct
SEQUENCE: 17
tgcatcattc cccatcgaaa gtgttcgaaa attggatacc cag            43
```

-continued

```
SEQ ID NO: 18            moltype = DNA   length = 28
FEATURE                  Location/Qualifiers
source                   1..28
                         mol_type = other DNA
                         organism = synthetic construct
SEQUENCE: 18
cgcttaagat tccgcggcat tagcgcga                                    28

SEQ ID NO: 19            moltype = DNA   length = 43
FEATURE                  Location/Qualifiers
source                   1..43
                         mol_type = other DNA
                         organism = synthetic construct
SEQUENCE: 19
ttacaattac catgggcgc gccatgggga atgatgcagg gtc                    43

SEQ ID NO: 20            moltype = DNA   length = 35
FEATURE                  Location/Qualifiers
source                   1..35
                         mol_type = other DNA
                         organism = synthetic construct
SEQUENCE: 20
ttacaattac catggcggaa tcttaagcga atatc                           35

SEQ ID NO: 21            moltype = DNA   length = 50
FEATURE                  Location/Qualifiers
source                   1..50
                         mol_type = other DNA
                         organism = synthetic construct
SEQUENCE: 21
ttacaattac catggcggaa tcttaagcga atatctccat agttgctaat            50

SEQ ID NO: 22            moltype = DNA   length = 45
FEATURE                  Location/Qualifiers
source                   1..45
                         mol_type = other DNA
                         organism = synthetic construct
SEQUENCE: 22
atatctccat agttgctaat atgttttgtt tcttccagcg ttgtt                45

SEQ ID NO: 23            moltype = DNA   length = 25
FEATURE                  Location/Qualifiers
source                   1..25
                         mol_type = other DNA
                         organism = synthetic construct
SEQUENCE: 23
cttcaatttt ttaaaccctc aaaat                                      25

SEQ ID NO: 24            moltype = DNA   length = 58
FEATURE                  Location/Qualifiers
source                   1..58
                         mol_type = other DNA
                         organism = synthetic construct
SEQUENCE: 24
ttacaattac catggcggaa tcttaagcga atatctccat agttgctaat aaattttg   58

SEQ ID NO: 25            moltype = DNA   length = 33
FEATURE                  Location/Qualifiers
source                   1..33
                         mol_type = other DNA
                         organism = synthetic construct
SEQUENCE: 25
tgcatcattc cccatcgaaa gtgttcgaaa att                             33

SEQ ID NO: 26            moltype = DNA   length = 25
FEATURE                  Location/Qualifiers
source                   1..25
                         mol_type = other DNA
                         organism = synthetic construct
SEQUENCE: 26
attttgaggg tttaaaaaat tgaag                                      25

SEQ ID NO: 27            moltype = AA   length = 360
FEATURE                  Location/Qualifiers
source                   1..360
                         mol_type = protein
                         organism = Glycine max
SEQUENCE: 27
```

-continued

```
MGNDAGSPQG PVTCGSWIRR PENLNLVVLG RSRRGNSCPS LLEIFSFDPK TTSLSTCPLT  60
TYVLEAEEGD PVAIAVHPSG DDFVCALSNG SCKLFELYGR ETNMKLLAKE LAPLQGIGPQ  120
KCIAFSVDGS KFAAGGLDGH LRIMEWPSMR VILDEPRAHK SVRDMDFSLD SEFLASTSTD  180
GSARIWKIED GVPLTTLSRN SDEKIELCRF SKDGTKPFLF CSVQKGDTSV TAVYEISTWN  240
KIGHKRLIRK SASVMSISHD GKYLSLGSKD GDICVVEVKK MQIYHYSKRL HLGTNIAYLE  300
FCPGERVLLT TSVEWGALVT KLTVPKDWKE WQIYLVLLGL FLASAVAFYI FFENSDSFWN  360
```